United States Patent [19]

Grunwell et al.

[11] 4,071,625

[45] Jan. 31, 1978

[54] 19-OXYGENATED-5α-ANDROSTANES FOR THE ENHANCEMENT OF LIBIDO

[75] Inventors: Joyce F. Grunwell, Hamilton, Ohio; Vladimir Petrow, Chapel Hill, N.C.

[73] Assignee: Richardson-Merrell Inc., Wilton, Conn.

[21] Appl. No.: 766,237

[22] Filed: Feb. 7, 1977

Related U.S. Application Data

[63] Continuation-in-part of Ser. No. 469,478, May 13, 1974.

[51] Int. Cl.$^2$ .......................... A61K 31/56; C07J 1/00

[52] U.S. Cl. .................................. 424/238; 424/241; 424/242; 424/243; 260/239.55 R; 260/239.55 C; 260/397.3; 260/397.4; 260/397.5

[58] Field of Search ................ 424/238, 241, 242, 243

[56] References Cited

PUBLICATIONS

Wolff et al., "Tetrahedron Letters, No. 23, (1966), p. 2507.

*Primary Examiner*—Elbert L. Roberts
*Attorney, Agent, or Firm*—William J. Stein; Eugene O. Retter; George W. Rauchfuss, Jr.

[57] ABSTRACT

Derivatives of 19-oxygenated-5α-androstanes are described which are useful in enhancing the libido and related psychic attitudes in mammals.

4 Claims, No Drawings

19-OXYGENATED-5α-ANDROSTANES FOR THE ENHANCEMENT OF LIBIDO

CROSS REFERENCE TO RELATED INVENTION

This application is a continuation-in-part of U.S. application Ser. No. 469,478, filed May 13, 1974.

SUMMARY OF THE INVENTION

This invention relates to the unexpected and surprising discovery that certain novel compounds, in addition to certain compounds previously described in the prior art, possess the property of enhancing a diminished libido in mammals without evoking any overt androgenic or estrogenic response upon the secondary sex structures. More particularly, the class of compounds which possess this novel utility is represented by the formula:

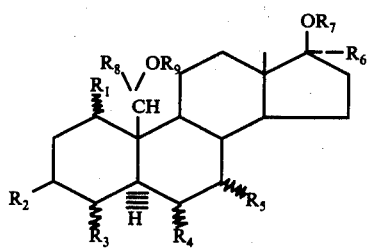

wherein $R_1$, $R_3$, $R_4$ and $R_5$ are hydrogen and methyl, $R_2$ is selected from the group consisting of $H_2$, oxo and $H(OR_{10})$, $R_6$ is selected from the group consisting of hydrogen, lower alkyl having from 1 to 6 carbon atoms, lower alkenyl having from 2 to 6 carbon atoms, lower alkynyl having 2 to 6 carbon atoms and when taken together with $OR_7$ is oxo, $R_7$ $R_9$ and $R_{10}$ are each selected from the group consisting of hydrogen, acyl having from 1 to 12 carbon atoms and an ether selected from the group consisting of lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms, and $R_8$ is hydrogen and when taken together with $OR_9$ is oxo.

DESCRIPTION OF THE PRIOR ART

The reduction of certain 19-hydroxy and 19-(substituted)hydroxy-$\Delta^4$-3-keto steroids for the preparation of the corresponding 5α and 5β-androstan-3-ones and androstan-3-ols is described by Knox et al., J. Org. Chem. 30, 2198 (1965). Structural assignments for these reduction products are presented based upon their optical rotatory dispersion curves.

Dauben and Ben-Efraim, J. Med. Chem., 11, 287 (1968) describe the preparation and solvolysis of 3β,19-dihydroxy-5α-androstan-17-one 3-acetate and 3β,19-dihydroxy-5α-androstan-17-one 3-acetate 19-tosylate. No utility is stated for these compounds.

Wolff and Cheng, Tetrahedron Letters, No. 23, 2507 (1966) compared the photochemical oxidation of 3β,17β-dihydroxy-androst-5-en-19-one with 3β,17β-dihydroxy-5α-androstan-19-one and its diacetate. No other use for these compounds is stated.

Hormones are generally recognized as being of significance in the biochemical regulation of the psyche and sexual behavior, cf., Hubble, Lancet, August 3, 1963, 209–214. However, applicants are not aware of any references which teach or suggest the unexpected properties possessed by the novel compounds of this invention. Furthermore, the compounds of this invention can be used without obtaining any overt, concomitant, somatic, androgenic or estrogenic side-effects.

DETAILED DESCRIPTION OF THE INVENTION

As shown in formula (I) above, the compounds of the present invention are 5α-androstan-19-ols, ethers or acylates and 5α-androstan-19-ones which can be substituted in the 1, 3, 4, 5, 6 and 17-positions of the steroid nucleus.

The symbols $R_1$, $R_3$, $R_4$ and $R_5$ represent either hydrogen or methyl. Thus, the 1, 4, 6 and 7-positions of the 5α-androstane nucleus can either remain unsubstituted, as when these various symbols represent hydrogen, or they may be individually substituted with a methyl group.

The symbol $R_2$ represents various substituents located at the 3-position of the 5α-androstane nucleus. Suitable substituents include two hydrogen atoms, an oxo group, and either a substituted or an unsubstitute dhydroxyl group. The substituted or unsubstituted hydroxyl group, represented by the symbol $OR_{10}$, can be present in either its alpha or beta configuration. When the symbol $R_{10}$ represents hydrogen, the free alcohol is, of course, delineated. When the symbol $R_{10}$ represents acyl, an acyl ester derived from a monobasic alkyl or aralkyl carboxylic acid having from 1 to 12 carbon atoms is present at the 3-position. The carboxylic acids from which these acylates are derived include saturated and unsaturated aliphatic acids as well as aromatic acids, as for example, acetic, propionic, butyric, isobutyric, valeric, isovaleric, caproic, caprylic, decanoic, dodecanoic, acrylic, crotonic, cyclobutanecarboxylic, cyclopentanecarboxylic, cyclopentenecarboxylic, cyclohexanecarboxylic, benzoic, toluic, naphthoic, ethylbenzoic, phenylacetic, naphthaleneacetic, phenylvaleric, cinnamic, phenylpropionic, p-propyloxyphenylpropionic and p-butyloxyphenylacetic acid. Finally, the 3-ethers are delineated when the symbol $R_{10}$ represents lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms.

The symbol $R_6$ represents the 17α-position and can be either a hydrogen atom or a saturated or unsaturated aliphatic chain having from 1 to 6 carbon atoms. Illustrative of such groups are straight or branched chain alkyl radicals, as for example, methyl, ethyl, propyl, isopropyl, butyl, sec-butyl, isoamyl, n-pentyl and n-hexyl. Illustrative of the alkenyl groups which can be present are the vinyl, allyl, 1-butenyl, 1-pentenyl, and 1-hexenyl radicals. Illustrative of the alkynyl groups which can be present are the ethynyl, 1-propynyl and 1-butynyl radicals. It should be noted that the symbols $R_6$ and $OR_7$ when taken together can also represent an oxo radical, thereby forming a class of substituted 5α-androstan-17-ones.

The symbol $OR_7$ represents various oxygenated substituents located at the 17β-position of the steroid nucleus. Suitable substituents include the hydroxyl group, an acyl ester and various lower alkyl, silyl, tetrahydropyranyl and various saturated or unsaturated cycloalkyl ethers. When $R_7$ represents hydrogen, the 17β-hydroxyl group is present. When $R_7$ represents acyl, a carboxylic acyl ester similar to those specifically enumerated for the 3-position is present. The class of 17β-ethers which are present belong to the same class of ethers previously enumerated for the 3-position.

The symbols $R_8$ and $R_9$ delineate the type of oxygenated function present at the 19-position. Thus, when $R_8$ and $R_9$ are both hydrogen the class of 5α-androstan-19-ols is defined. The symbol $R_9$ also represents an acyl group having from 1 to 12 carbon atoms, thereby describing a class of esters similar to those specifically enumerated for the 3-position, i.e., 5α-androstan-19-ol acylates. The class of 19-(ether)-5α-androstanes is described when the symbol $R_9$ represents an ether. The various ether groups which may be represented are similar to those described for the 3 and 17β-positions and include the class of lower alkyl, silyl, tetrahydropyranyl and saturated or unsaturated cycloalkyl ethers. The class of 5α-androstan-19-ones is defined when the symbols $R_8$ and $OR_9$ are taken together to form the oxo group.

A preferred class of compounds included within the scope of the present invention includes the 17β-ethers of 5α-androstane-3,19-dione. These compounds are delineated where the symbol $R_7$ represents an ether selected from the group consisting of lower alkyl having from 1 to 3 carbon atoms, trialkylsilyl, in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms, and, in addition, the symbol $R_2$ is oxo and the symbol $R_8$ when taken together with $OR_9$ is oxo. Illustrative species encompassed within this preferred class of compounds include 17β-methoxy-1α-methyl-5α-androstane-19-dione, 1α,-4α,17α-trimethyl-17β-triethylsiloxy-5α-androstane-3,19-dione, 4α, 6β-dimethyl-17β-(2'-tetrahydropyranyloxy)-5α-androstane-3,19-dione, 17β-(1'-cyclohexenyloxy)-17α-vinyl-5α-androstane-3,19-dione, 6β-methyl-17β-(triphenylsiloxy)-5α-androstane-3,19-dione, 17αethynyl-17β-(1'-methoxycyclohexyloxy)-1α,7α-dimethyl-5α-androstane-3,19-dione, 17;62 -propoxy-5α-androstane-3,19-dione, 1β, 4α,6β-trimethyl-17α-hexyl-17β-(4'-tetrahydropyranyloxy)5α-androstane-3,19-dione, 17β-(1'-cyclopentenyloxy)-5α-androstane-3,19-dione, 17β-(1'-ethoxycyclopentyloxy)-7α-methyl-17α-(1'-propenyl)-5α-androstane-3,19-dione, 1α, 4α, 6β, 7α-tetramethyl-17β-tributylsiloxy-5α-androstane-3,19-dione and 17β-ethoxy-17α-ethyl-4α-methyl-5α-androstane-3,19-dione.

Another preferred group of compounds are the 17α-ethers of 19-hydroxy-5α-androstan-3β-one. These compounds are delineated where the symbol $R_7$ is an ether selected from the group consisting of lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms. In addition, the symbols $R_8$ and $R_9$ are both hydrogen and the symbol $R_2$ is oxo. Illustrative species encompassed within this preferred class of compounds include 19-hydroxy-17β-methoxy-7;60 -methyl-5α-androstan-3-one, 19-hydroxy-1β, 4α, 6β, 7α-tetramethyl-17β-triethylsiloxy-5α-androstan-3one, 19-hydroxy-7α, 17;60 -dimethyl-17β-(2'-tetrahydropyranyloxy)-5α-androstan-3one, 17β-(1'-cyclohexenyloxy)-17α-ethenyl-19-hydroxy-1α,4α,6β-trimethyl-5α-androstan-3one, 19-hydroxy-17β-triphenylsiloxy-5α-androstan-3-one, 17α-ethynyl-19-hydroxy-17β-(1'-methoxycyclohexyloxy)-1α,7α-dimethyl-5α-androstan-3one, 19-hydroxy-6β-methyl-17β-propoxy-5α-androstan-3-one, 17α-hexyl-19-hydroxy-17;62 -(4'-tetrahydropyranyloxy)-5α-androstan-3-one, 17β-(1'-cyclopentenyloxy)-19-hydroxy-4α,6β-dimethyl-5α-androstan-3-one, 17β-(1'-ethoxycyclopentyloxy)- 19-hydroxy-17α-(1'-propenyl)-5α-androstan-3-one, 1,4α-dimethyl-17;62 -tributylsiloxy-19-hydroxy-5α-androstan-3-one and 17;62 -ethoxy-17;60 -ethyl-19-hydroxy-1β-methyl-5α-androstan-3-one.

The novel alkyl ethers are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as silver oxide or barium oxide in polar, aprotic solvents as for example, dimethylformamide, dimethyl sulfoxide and hexamethylphosphoramide. In order to prepare the novel silyl ethers, the hydroxyl groups can be silylated by reaction with silylating agents such as trialkylchlorosilane, triarylchlorosilane and N-trialkylsilylacetamide in the presence of an amine base such as triethylamine or pyridine.

The 2-tetrahydropyranyl ethers are prepared from the corresponding hydroxy steroids by reaction with dihydropyran in the presence of an acid catalyst, as for example, hydrochloric acid, p-toluenesulfonic acid or phosphorous oxychloride. The 4-tetrahydropyranyl ethers are prepared by reacting the hydroxy steroid, 4-bromotetrahydropyran and a base such as sodium hydride together in a polar aprotic solvent such as dimethylformamide, dimethylsulfoxide or hexamethylphosphoramide.

The 1-alkoxycycloalkoxy ethers are prepared by reacting the hydroxy steroids with a loweralkylketal of a cycloalkanone or the lower alkylenol ether of a cycloalkanone or mixture of these reagents in the presence of an acidic catalyst such as p-toluenesulfonic acid, pyridine hydrochloride, pyridine p-toluenesulfonate. The reaction is generally conducted in a solvent such as dioxane, methylene chloride, ether or t-butanol at a temperature less than 70° C., and preferably at 25° C. The preparation of suitable cycloalkyl derivatives is achieved using such reagents as cyclopentanone diethylketal, cyclohexanone dimethylketal, 1-methoxy-1-cyclopentene or 1-ethoxy-1-cyclohexene. Following essentially the same procedure, the 1-cycloalkenyl ethers are prepared directly using, however, higher boiling solvents so that the reaction temperature is above 70° C. Suitable solvents include benzene, toluene and dimethylformamide. Alternatively, the 1-cycloalkenylethers can be prepared via a pyrolysis of the isolated 1-alkoxycycloalkoxysteroid in the presence of a trace of an organic base such as pyridine utilizing a high boiling solvent such as benzene or dimethylformamide.

The acyl groups are introduced by standard methods known to those skilled in the art such as the reaction of the hydroxysteroid with an acid anhydride or acid chloride in the presence of a base such as pyridine.

Reduction of the 19-hydroxy-5α-androstan-3ones with metal hydrides such as lithium aluminum hydride, lithium tri-t-butoxyaluminum hydride and sodium borohydride produces the 5α-androstane-3β,19-diol. The use of a highly hindered lithium or potassium trialkylborohydride, such as potassium tri-sec-butylborohydride, results in the formation of the corresponding 3α-alcohol, namely the 5α-androstane-3α,19-diol.

The 19-aldehyde is prepared from the corresponding 19-alcohol utilizing one of two procedures. A Jones oxidation, utilizing exactly one equivalent of reagent and conducted in the cold, preferably between −20° and 10° C., yields the aldehyde without overoxidation to the corresponding 19-acid. The Pfitzner-Moffatt procedure, utilizing dimethylsulfoxide, dicyclohexylcarbodiimide, pyridine and trifluoroacetic acid in benzene at room temperature, produces the 19-aldehyde from the corresponding 19-alcohol.

The 3-deoxy series of 5α-androstan-19ols is prepared by converting the 19-hydroxy-5α-androstan-3-one to its 3-ethylenethioketal by reaction with ethanedithiol and an acid catalyst, such as p-toluenesulfonic acid or boron trifluoride etherate. The ethylenethioketal is then desulfurized with Raney nickel to yield the 5α-androstan-19-ol. A Jones oxidation or Pfitzner-Moffatt oxidation results in the formation of the corresponding 5α-androstan19-one.

Hydrogenation of 19-hydroxy-5-androstenes by means of 10% palladium on charcoal results in good yields of the corresponding 19-hydroxy-5α-androstanes. Suitable steroid substrates which fulfill the 5-ene requirement for stereoselectivity during the reduction include 3β,19-dihydroxy-5-androstenes, 19-hydroxy-5-androsten-3-ones, 19-hydroxy-5-androsten-3-one 3-cyclic ethyleneketal and 3-alkoxy-3,5-androstadien-19-ols. Typical reduction conditions utilize 2-10parts of the steroid substrate to 1 part catalyst with methanol or ethanol as solvent and hydrogen pressures ranging from 1 to 3 atmospheres. In this manner 1β,17α-dimethyl-5-androstene-3β,17β,19-triol, 7α-methyl-19-tetrahydropyranyloxy-5-androsten-3β,17β-diol and 6α-methyl-3β,19-dihydroxy-5-androsten-17-one are reduced to 1β,17α-dimethyl-5α-androstane-3β,17β,19-triol, 7α-methyl-19-tetrahydropyranyloxy-5α-androstan-3β,17β-diol and 6α-methyl-3β,19-dihydroxy-5α-androstan-17-one, respectively. 19-Hydroxy-1α-methyl-4-androstene-3,17-dione is converted to its cyclic ethyleneketal by heating at reflux temperatures with p-toluenesulfonic acid and ethyleneglycol in benzene. The ketal which forms is then reduced and hydrolyzed to form 19-hydroxy-1α-methyl-5α-androstan-3,17-dione. 17β,19-Di(trimethylsiloxy)-4-androsten-3-one can be converted to the methyl enol ether by the action of trimethylorthoformate, p-toluenesulfonic acid and methanol in tetrahydrofuran. The 3-methoxy-3,5-diene which forms is then catalytically reduced to yield 17β,19-di(trimethylsiloxy)-5α-androstan-3-one. The ethylenol ether of 19-hydroxy-4-androsten-3,17-dione acetate can also be reduced to yield 19-hydroxy-5α-androstane-3,17-dione acetate.

A Birch reduction of 19-hydroxy-4-androsten-3-ones with lithium in liquid ammonia and ammonium chloride forms the corresponding 19-hydroxy-5β-androstan-3-one. However, when the 19-hydroxy group is blocked as an ester or ether, or is replaced by an 19-aldehyde, then the Birch reduction forms the corresponding 5α-androstan-3-one. Under these lithium-ammonia conditions 7α-methyl-17β,19-di(triphenylsiloxy)-4-androsten-3-one, 17α-ethinyl-17β,19-di(2′-tetrahydropyranyloxy)-4-androsten-3-one and 4-androstene-3,17,19-trione can be reduced to 7α-methyl-17β,19-di(triphenylsiloxy)-5α-androstan-3-one, 17α-ethinyl-17β,19-di(2′-tetrahydropyranyloxy)-5α-androstan-3-one and 5α-androstane-3,17,19-trione, respectively.

The 1,4,6, and 7-methyl 5α-androstanes of the present invention are prepared by a reduction of the corresponding 19-substituted 4or 5-androstenes as described above. These 19-substituted intermediates used as starting materials are prepared by the following routes.

Reaction of dichlorodicyanobenzoquinone with 19-hydroxy-4-androsten-3-ones in refluxing dioxane or methylenechloride for a period of 24 to 72 hours produces the corresponding 19-hydroxy-1,4-androstadien-3-one. Two restrictions in this sequence are necessary, however. First, the 19-hydroxy group must be protected as an ester or an ether in order to avoid aromatization. Secondly, the 1-position must possess an axial hydrogen atom for elimination. Thus, the 1α-methyl androstene is not reactive in this procedure although the 1β-methyl androstane is. Following this procedure 17β,19-dihydroxy-7α-methyl-4-androsten-3-one dipropionate is converted to 17β,19-dihydroxy-7α-methyl-1,4-androstadien-3-one dipropionate. Similarly, 19-hydroxy-6α-methyl-4-androsten-3,17-dione acetate forms 19-hydroxy-6α-methyl-1,4-androstadien-3,17-dione acetate and 1β-methyl-19-tetrahydropyranyloxy-4-androsten-3,17-dione forms 1-methyl-19-tetrahydropyranyloxy-1,4-androstadien-3,17-dione.

The 1α-methyl-19-substituted-androst-4-enes are produced by reacting the corresponding androsta-1,4-dien-3-ones so obtained with dimethyllithium copper. Methylation is preferably conducted by adding the androsta-1,4-dien-3-one dissolved in an inert solvent to a solution of dimethyllithium copper in the same or a different inert solvent. Suitable inert reaction solvents include methylene chloride, tetrahydrofuran, dioxane, hexane, benzene with diethyl ether being the solvent preferred. The reaction is conducted at temperatures between −75° C. and 20° C. with a temperature range of from about −5° C. to 0° C. being preferred. The ratio of reactants is not critical, but at least 2 molar equivalents of dimethyllithium copper must be present for each conjugate addition. The presence of free hydroxyl groups will, of course, require additional equivalent amounts of the organometallic reagent. Following this procedure, 19-hydroxyandrosta-1,4-diene-3,17-dione propionate can be converted to 19-hydroxy-1α-methyl-androst-4-en-3,17-dione propionate.

The 1β-methyl-19-substituted-4-androsten-3-ones are synthesized in the manner of Simmons and Smith by treatment of a 19-substituted-androsta-1,5-dien-3β-ol with methylenediiodide and a zinc-copper couple to form the 19-substituted-1β,2β-methylene-androst-5-en-3-ol. The presence of the 3β-alcohol as well as the 19-alcohol direct the insertion to the beta side. The 1β,2β-methylene-3β-ol is then oxidized to a 3-one and the cyclopropyl ring cleaved by acid or base to form the 19-substituted-1β-methyl-4-androsten-3-one. Typically a mixture of zinc-copper couple, iodine and methylenediiodide in an inert solvent such as diethylether, tetrahydrofuran, dioxane or diglyme is heated with an infrared lamp for thirty minutes. The steroid, also in an inert solvent as above, is added and the mixture heated from 25° to 100° for a period of from 30 minutes to 72 hours. Generally, reflux temperatures of the solvents employed combined with a 24 hour reflux period are sufficient, and the Simmons-Smith reagent added in a 5 to 10 fold excess. The oxidation of the 3-alcohol is readily achieved by means of various oxidizing agents. Illustrative oxidizing agents are the Jones reagent, $CrO_3$·pyridine complex (Sarett reagent), and the Cornforth reagent. However, in the event that the 19-alcohol is not suitably protected, it will also be oxidized. Finally, the resulting $1\beta,2\beta$-methylene ring is cleaved by refluxing with zinc in acetic acid to form the $1\beta$-methyl group. In this manner 19-tetrahydropyranyloxy-1,5-androstadien-3,17-diol is converted to $1\beta$-methyl-19-hydroxy-4-androstene-3,17-dione.

Methylation of 19-hydroxy-4-androsten-3-ones using Atwater3 s procedure, N.W. Atwater, J. Am. Chem. Soc. 79, 5315 (1957), of slowly adding methylchloride to a refluxing solution of the ketone in t-butanol, containing a slight excess of potassium t-butoxide, produces the 19-hydroxy-4-methyl-4-androsten-3-ones in fair yields. Following this procedure 19hydroxy-7α-methyl-androst-4-ene-3,17-dione and $17\beta,19$-hydroxy-$1\alpha,7\alpha$-dimethyl-androst-4-en-3-one can be converted to 19-hydroxy-4,7α-dimethyl-androst-4-ene 3,17-dione and $17\beta,19$-dihydroxy-$1\alpha,4,7\alpha$-trimethyl-androst-4-en-3-one, respectively.

Alternatively, the 19-hydroxy-4-androsten-3-one can be selectively thiomethylated at the 4-position with formaldehyde and a thiol under basic conditions. Benzylmercaptan is the preferred thiol. Desulphurisation of the intermediate 19-hydroxy-4-phenylthiomethyl-4-androsten-3-one leads to the monomethylated 19-hydroxy-4-methyl-4-androsten-3-one in good yield. Alternatively, 19-hydroxy-4-androsten-3-ones in which the 19-hydroxy group is blocked as an ester or ether or 4-androstene-3,19-diones will undergo reductive alkylation with lithium in liquid ammonia and methyl iodide to form the 19-substituted-4-methyl-5α-androstan-3-one.

Treatment of a 5α,6α-epoxyandrostane-3,19-diol or a 3,3-ethylenedioxy-5α,6α-epoxyandrostan-19-ol with methylmagnesium bromide in dry solvents such as diethyl ether, tetrahydrofuran, benzene or toluene at temperatures between 0° to 100° C., results in epoxide cleavage to yield the corresponding 6β-methyl-androstane-5α,19-diols. The corresponding 3-alcohol can be oxidized or the ketal group hydrolyzed with hot acetic acid or dilute aqueous methanolic mineral acid to form the 5α-hydroxy-6βmethyl-3-ketone. Dehydration of the β-hydroxy ketone with sodium hydroxide in hot aqueous methanol is accompanied by inversion at position 6 to form the 6α-methylandrost-4-en-3-one. In this manner the compounds $17\beta,19$-dihydroxy-6α-methyl-4-androsten-3-one, $17\beta$-hydroxy-6α, 17α-dimethyl-4-androstene-3,19-dione are prepared starting with 3,3-ethylenedioxy-5α,6α-epoxyandrostan-17,19-diol and 5α,6α-epoxy-17α-methylandrostan-$3\beta,17\beta,19$-diol, respectively.

The 7α-methyl-4-androstene-3,19-diones are produced by alkylating the corresponding 4,6-androstadien-3,19-dione with dimethyllithium copper in an inert solvent such as diethyl ether, tetrahydrofuran, hexane or mixtures of such solvents at temperatures ranging from −78° to 25° C. Tetrahydrofuran is the preferred solvent and temperatures between −5° to 10° C. provide optimum results. Quenching the initially formed enolate anion by means of a weak protonating agent such as a saturated solution of ammonium chloride, oxalic acid or boric acid provides the 7α-methyl-5-androstene-3,19-diones. Quenching the enolate with a strong protonating agent such as hydrochloric acid provides the 7α-methyl-4-androstene-3,19-diones.

Alternatively, 7α-methyl-4-androstene-3,19-dione can be prepared by either an acid or base catalyzed isomerization of the corresponding 7α-methyl-5-androstene-3,19-dione. Suitable acid catalysts include hydrochloric acid, sulfuric acid, p-toluenesulfonic acid and acetic acid, and they can be employed in such solvents as methanol, ethanol, dioxane, tetrahydrofuran and methylenechloride. Suitable base catalysts for this isomerization include sodium hydroxide or sodium methoxide in an alcohol solvent such as methanol. Following this procedure $1\alpha,7\alpha$-dimethyl-4-androstene-3,17,19-trione, 7α-methyl-$17\beta$-(2'-tetrahydropyranyloxy)-4-androstene-3,19-dione and $17\beta$-hydroxy-$7\alpha,17\alpha$-dimethyl-4-androstene-3,19-dione are prepared starting with 1α-methyl-4,6-androstadiene-3,17,19-trione, $17\beta$-(2'-tetrahydropyranyloxy)-4,6-androstadiene-3,19-dione and $17\beta$-hydroxy-4,6-androstadiene-3,19-dione.

The 7α-methyl-4-androstene-3,19-diones so prepared can be reduced to the diols with reagents such as lithium aluminum hydride, lithium tri-t-butoxyaluminumhydride, sodium borohydride or potassium borohydride. The 3-hydroxyl group can then be selectively oxidized with reagents specific for allylic alcohol oxidation, such as activated manganese dioxide or dichlorodicyanobenzoquinone. Following this procedure the 19-hydroxy-4-androsten-3-one can be prepared. Similarly, 1α, 7α-dimethyl-4-androstene-3,17,19-trione can be converted to $1\alpha,7\alpha$-dimethyl-4-androstene-$3\beta$, $17\beta,19$-triol and then to $17\alpha,19$-dihydroxy-$1\alpha,7\alpha$-dimethyl-4-androsten-3-one. In the same fashion, 7αmethyl-$17\beta$-(2'-tetrahydropyranyloxy)-4-androstene-3,19-dione can be converted to 7α-methyl-$17\beta$-(2'-tetrahydropyranyloxy)-4-androstene-$3\beta,19$-diol and then to 19-hydroxy-7α-methyl-$17\beta$-(2'-tetrahydropyranyloxy)-4-androsten-3-one.

Both the 19-hydroxy-5-androsten-$3\beta$-ols and the 19-hydroxy-4-androsten-3-ones used in the present invention as intermediates are prepared by the methods described in Vol. II of Organic Reactions in Steroid Chemistry, Edited by J. Fried and J. A. Edwards, p. 237–87, van Nostrand Reinhold Company, N.Y., (1972). One route to these compounds proceeds from the 5α-halogen-$6\beta,19$-ether intermediates. These latter compounds are prepared from their corresponding 5,6-unsaturated steroids by the addition of a hypohalous acid to form the 5α-halogen -$6\beta$-carbinols, which are subsequently cyclized by means of lead tetraacetate or the $6\beta$-hypohalites are decomposed to yield the desired 5α-halogen-$6\beta$,19-ethers. Thus, for example, $3\beta,17\beta$-dihydroxy-5-androstene diacetate is converted to 5α-bromo-$3\beta,6\beta,17\beta$-trihydroxyandrostane 3,17-diacetate by means of N-bromoacetamide and perchloric acid. Lead tetraacetate or hypoiodide converts this intermediate to 5α-bromo-$3\beta,17\beta$-dihydroxy-$6\beta,19$-oxidoandrostane 3,17-diacetate. In the same manner $3\beta,19$-oxidoandrostane 3,17-diacetate. In the same manner $3\beta$-hydroxyandrost-5-en-17-one acetate can be converted to 5α-bromo-$3\beta,6\beta$-dihydroxyandrostan-17-one 3-acetate. A lead tetraacetate or hypoiodite oxidation converts this latter compound into 5α-bromo-$3\beta$-hydroxy-$6\beta,19$-oxidoandrostane-17-one acetate. This 17-ketone reacts with an organometallic reagent such as methylmagnesium bromide or lithium acetylide to form the desired 17α-alkylated 17β-hydroxy derivative.

The 3-oxo-4-ene group can be introduced into the steroid molecule by oxidizing the 3β-hydroxy-5α-halo-6β,19-oxido intermediate with an oxidizing reagent such as chromium trioxide. Subsequent dehydrohalogenation using pyridine or sodium acetate in methanol results in the formation of the corresponding 6β,19-oxidoandrost-4-en-3-one. This 6β,19-ether is reductively cleaved by means of such reagents as zinc and isopropanol, zinc and ethanol, zinc and acetic acid or lithium and ammonia to form the desired 19-hydroxyandrost-4-en-3-one. Cleavage with zinc in acetic acid furnishes the 19-acetate while zinc in alcohol furnishes the free 19-alcohol. Alternatively, the 3β-acetoxy5α-bromo-6β,19-oxido androstane intermediate can be converted to the 5-androstene-3β,19-diol 3-acetate or 3,19-diacetate by the action of zinc in alcohol or zinc in acetic acid. Cleavage with zinc and acetic acid furnishes the 3,19-diacetate while zinc and alcohol cleavage furnishes the 3-acetate. This selectivity is useful in preparing the 19-oxygenated derivatives in the presence of the 3-acetate. In addition to providing the 19-hydroxyandrostane starting materials for either introduction of methyl groups at 1,4,6,7 either singly or in combinations, the above reaction sequence can be carried out with the methyl groups already present in these positions to produce the compounds of this invention directly.

An alternative route to the 19-hydroxyandrost-4-en3-ones proceeds from the 6β,19-oxido-3α,5α-cycloandrostanes as intermediates. These compounds are in turn prepared by a lead tetraacetate or hypoiodite oxidation upon the corresponding 6β-hydroxy-3α,5α-cycloandrostane, an i-steroid. Heating the 6β,19-ether in a solvent such as dimethylsulfoxide with benzoylperoxide results in cleavage and the direct formation of the 19-hydroxyandrost-4-en-3-one. Alternatively, the 6β,19-ether can be cleaved to the corresponding 3β,19-dihydroxy-5-androstene using sulfuric acid in an aqueous acetone solution. This compound is then oxidized to the desired 19-hydroxyandrost-4-en-3-one by means of an Oppenauer oxidation.

The mixed alcohols, esters, ethers, aldehydes and ketones of the present invention are prepared by means of selective oxidation, reduction, protection and hydrolysis reaction sequences employing both the intermediate androst-4-enes and androst-5-enes. Thus, 5-androstene-3β,19-diol diester can be selectively hydrolyzed to the 19-monoester by a 1 to 2 hour reflux in a 10% aqueous methanol solution containing one equivalent potassium bicarbonate. In this manner 3β,19-dihydroxy-5-androsten-17-one dipropionate can be hydrolyzed to 3β,19-dihydroxy-5-androsten-17-one 19-propionate.

A 17β,19-dihydroxy-4-androsten-3-one diester can be selectively hydrolyzed to the 17-monoester by refluxing for about 1 hour in a 10% aqueous methanol solution containing one equivalent of sodium bicarbonate. In this manner 17β,19-dihydroxy-4-methyl-4-androsten-3-one dipropionate and 17β,19-dihydroxy-4-androsten-3-one diacetate are converted to 17β,19-dihydroxy-4-methyl-4-androsten-3-one 17-propionate and 17β,19-dihydroxy-4-androsten-3-one 17-acetate, respectively.

A 19-hydroxy-4-androstene-3,17-dione can be selectively reduced to a 17β,19-dihydroxy-4-androsten-3-one by the action of potassium borohydride in ethanol at −10° C. to 0° C. generally employing reaction times of less than 5 hours. In this manner, 6α-methyl-19-(2'-tetrahydropyranyloxy)-4-androstene-3,17-dione and 19-ethoxy-1α-methyl-4-androstene-3,17-dione can be selectively reduced to 17β-hydroxy-6α-methyl-19-(2'-tetrahydropyranyloxy)-4-androsten-3-one and 19-ethoxy-17β-hydroxy-1α-methyl-4-androsten-3-one, respectively.

A 4-androstene-3β,17β,19-triol can be selectively oxidized to a 17β,19-dihydroxy-4-androsten-3-one by activated manganese dioxide in an inert solvent such as methylene chloride and chloroform at temperatures below 25° C. Elevated temperatures promote oxidation at the 19-position. This selective allylic oxidation is also accomplished by the action of dichlorodicyanobenzoquinone on the triol in solvents such as dioxane or methylene chloride. The preferred temperature is below 25° C. and typical reaction times range from about 1 to about 18 hours. In this fashion, 1β-methyl-4-androstene-3β,17β,19-triol and 17α-ethinyl-4-androstene-3β,17β,19-triol are converted to 17β,19-dihydroxy-1β-methyl-4-androsten-3-one and 17β-ethinyl-17β,19-dihydroxy-4-androsten-3-one, respectively.

The reductive cleavage of the acetates of 5α-bromo6β,19-oxidoandrostan-3β-ols by the action of zinc in ethanol results in the formation of the 5-androstene- 3β,19-diols 3-acetate. In contrast thereto, the action of zinc in acetic acid on these same acetates of 5α-bromo- 6β,19-oxidoandrostan-3β-ols provides the 5-androstene- 3β,19-diols diacetates. Selective potassium bicarbonate hydrolysis on these diacetates, as discussed above, produces the corresponding 5-androstene-3β,19-diols 19- acetate.

More particularly, a zinc and acetic acid cleavage of 5α-bromo-3β-hydroxy-6β,19-oxidoandrostan-17-one results in the formation of 3β,19-dihydroxy-5-androsten-17-one diacetate. Lithium tri-t-butoxyaluminum hydride reduction then results in the preparation of 5-androstene-3β,17β,19- triol 3,19-diacetate. The 17β-hydroxy group can now be converted to an ether using standard procedures to form, for example, 17β-methoxy-5-androstene-3β,19-diol diacetate or 17β-(4'-tetrahydropyranyloxy)-5-androstene-3β,19-diol diacetate. A catalytic hydrogenation then furnishes the corresponding 5α-androstane. Basic hydrolysis subsequently cleaves the esters to form the free 17-ether diols. In this manner the compounds, 17β-methoxy-5α-androstane-3β,19- diol and 17β-(4'-tetrahydropyranyloxy)-5α-androstane-3β,19-: diol can be prepared. Oxidation results in the formation of the corresponding diones. Etherification thereof furnishes the mixed triethers.

Hydrolysis of the 17-ether-5-androstene-3β,19-diol diacetate with potassium bicarbonate results in the formation of the 19-monoacetate. Catalytic reduction results in the preparation of the corresponding 5α-androstanes, as, for example, 17β-methoxy-5α-androstane-3β,19-diol 19-acetate and 17β-(4'-tetrahydropyranyloxy)-5α-androstan- 3β,19-diol 19-acetate. Subsequent etherification of the 3-hydroxy group results in the preparation of the 3,17- mixed ethers-5α-androstan-19-ol acylate. Oxidation of the 3-hydroxy group furnishes the 19-hydroxy-17-ether-5α- androstan-3-ones.

19-Hydroxy-4-androstene-3,17-diones are etherified in the manner described above to produce the 19-ether-4- androstene-3,17-diones. A Birch reduction results in the preparation of the 19-ether-5α-androstane-3,17-diones which can be further reduced with lithium aluminum hydride, lithium trialkoxyaluminum hydride or sodium borohydride to form the corresponding 3,17-dihydroxy analogues. Thus, for example, 19-trimethylsiloxyandrost-4-ene-3,17-dione, 19-tetrahydropyranyloxy-androst-4-ene-3,17-dione, 19-methoxyandrost-4-ene-3,17-dione are converted by the above procedures to 19-trimethylsiloxy-5α-androstane-3β,17β- diol, 19-tetrahydropyranyloxy-5α-androstane-3β,17β-diol and 19-methoxy-5α-androstane-3β,17β-diol respectively.

17β,19-Dihydroxyandrost-4-en-3-ones can be similarly etherified to form the 17,19-diethers. A Birch reduction followed by the ketone reductions described above yields the 17β,19-diether-5α-androstan-3-ols. Thus, for example, 17β,19-dihydroxyandrost-4-en-3-one can be converted to 17β,19-di-triphenylsiloxyandrost-4-en-3-one or 17β,19-di-(1′-methoxy-1′-cyclopentyloxy)androst-4-en-3-one. These compounds are then reduced first with lithium in ammonia to form the 17β,19-di-triphenylsiloxy-5α- androstan-3-one and 17β,19-di-(1′-methoxy-1′-cyclopentyl- oxy)-5α-androstan-3-one, respectively. A lithium aluminum hydride reduction in an ether or tetrahydrofuran solution then results in the preparation of 17β,19-di-triphenylsiloxy-5α-androstan-3β-ol and 17β,19-di-(1-methoxy-1- cyclopentyloxy)-5α-androstan-3β-ol, respectively.

The 3,17,19-triethers are readily available from the corresponding 5α-androstane-3β,17β,19-triols in the manner previously described. The 3,17-diethers can also be prepared in this manner. For example, 19-hydroxyandrost- 4-ene-3,17-dione can be acetylated in the usual manner with acetic anhydride and pyridine to form the corresponding 19-acetate.

Conversion to the enol ether and subsequent catalytic hydrogenation furnishes the 19-hydroxy-5α-androstane-3,17- dione acetate. The 3,17-diones are then selectively reduced using lithium tri-t-butoxy aluminum hydride to form 5α-androstane-3β,17β,19-triol 19-acetate. Etherification of positions 3 and 17 in the aforementioned manner results in the preparation, for example, of 3β,17β- (1-cyclopentenyloxy)-5α-androstan-19-ol acetate or 3β,17β- ditetrahydropyranyloxy-5α-androstan-19-ol acetate. Cleavage of these 19-acetates with lithium aluminum hydride results in the formation of 3β,17β-(1-cyclopentenyloxy)- 5α-androstan-19ol and 3β,17β-ditetrahydropyranyloxy-5α- androstan-19-ol, respectively. Mixed ether/esters are prepared by suitable combinations of the general methods described above. For example, 17β,19-dihydroxyandrost- 4-en-3-one can be acetylated to form the diacetate, and then catalytically reduced through the enol ether to form the 17β,19-dihydroxy-5α-androstan-3-one diacetate. The remaining 3-ketone can be reduced to the corresponding alcohol and etherified to yield a 3-ether-17,19- diacetate. Cleavage of the 17,19-diacetate to the corresponding alcohols as previously described results in the preparation, for example, of 3β-methoxy-5α-androstane-17β,19-diol and 3β-(1-ethoxycyclohexyloxy)-5α-androstane- 17β,19-diol, respectively.

The compounds of this invention, as represented by formula (I) above, are useful in modulating the behavior of normal, non-hostile animals when placed in contact with hostile aggressive animals. Hostile aggression in animals can be induced by a prolonged isolation of individual animals in the dark. Modulation of the behavioral response in the treated, normally non-hostile animals towards the aggressive animals broadly suggests their use in humans for certain psychasthenic syndromes and related conditions of mental health.

Applicants have made the further important discovery that the 19-oxygenated-5α-androstanes described in formula (I) above, enhance the libido of mammals. Illustrative of the term mammals are such species as mice, rats, guinea pigs, rabbits, ferrets, dogs, cats, cows, horses and primates including man. The expression "libido" as used herein refers, in general, to the sexual interest and sexual drive of mammals. However, as used herein, the expression "libido" is also intended to include certain psychic attitudes in primates, particularly man, associated with a diminished libido, relating to the mental and emotional well-being of an individual.

The mental well-being of concern herein is reflected in the degree of mental activity, mental awareness, drive and energy of the individual. The emotional well-being of concern herein is exhibited in the creativity, enthusiasm and social awareness of the individual. Individuals whose psychic attitudes are diminished are apt to feel "down" or depressed and morose. Individuals having enhanced psychic attitudes are more alert and perceptive; they are better able to perform routine repetitive mental tasks.

Libido is generally recognized to be the result of a complex interaction of factors in which genetic, anatomic, neurologic, psychologic and biochemical factors all play prominent roles. The exact mechanism by which the conpounds of this invention achieve their effect is not understood except to the extent that it is known to be attributable to some form of biochemical mechanism. Secretions of the endocrine glands are known to affect the psyche. Thus, there is a degree of positive correlation between testosterone blood level changes and dominant or aggressive behavior. Testosterone infusion is also known to improve mental performance in repetitive mental tasks. It has recently been suggested that a dysgenesis of androgen steroids may have a bearing in schizophrenia, cf., Alias, A. G., Lancet, 1248-9, No. 2 (1972).

The fact that libido in both men and women bears a relationship to the endocrine system, and more particularly, to the steroidal hormones associated therewith, has been previously reported, and is clinically recognized. Physicians are often confronted with patients having a variety of symptoms including those of a diminished libido and related psychasthenia, which may be either organic or psychosomatic in origin. Heretofore, therapy employing the administration of testosterone and its esters, or the orally active 17-methyltestosterone has frequently been employed. Adjunctive androgen therapy is also recommended for the restoration of libido in women with certain gynecologic disturbances and in women who have had oophorectomy and bilateral adrenalectomy. Similarly, androgen therapy has been used to restore libido in impotent men whose impotence has been associated with an endocrine malfunction or insufficiency, as for example, in Addison's disease, castration diabetes mellitus, eunuchoidism, feminizing interstitial-cell tumors, infantilism and obesity.

Although in some patients such treatment has been effective, it has generally proven to be disappointing due to the physiological side effects of the androgen which soon become apparent. In the female, therapeutic doses of testosterone can produce a virilizing effect including hirsuitism, hoarseness or deepening of the voice and an increase in uterine weight. In the male such symptoms as an increased growth of body hair, an increase in weight of the ventral prostate, enlarged siminal vesicles, increased seminal fluid and sterility have been observed. In striking contrast to the androgens previously utilized for this purpose, the libido of mammals and the psychic attitudes associated therewith in primates are enhanced without any overt, concomitant, androgenic, somatic side-effects upon the sex accessory structures by the administration of the androst-4-en-19-ones described in formula (I) above.

The castrated rhesus monkey is a useful primate model in which to demonstrate and observe enhanced libidinous behavior. However, the size and temperament of these animals, plus the expense of maintaining large monkey colonies, makes them unsuitable for ordinary routine screening of large numbers of compounds. Whereas the castrated rat is a useful model for the observation of libidinous behavior, the castrated-adrenalectomized rat provides an even higher degree of correlation with primates such as the castrated monkey. The castrated or the castrated-adrenalectomized rat is a more practicable and manageable animal model that can be accommodated in the large numbers required for the successful testing of compounds and are the standard experimental animals employed for the evaluation of chemical compounds by those skilled in the art.

Administration of the 19-oxygenated-5α-androstanes above to castrated-adrenalectomized rats results in both an increase in the number and frequency of mounts, intromissions and ejaculations as compared with castrated control animals. Notably, there is observed a decrease in the refractory period following emission. This refractory or post-ejaculatory period for the rat refers to the time period following emission and prior to remounting. During this period the male rat is sexually inert and will even resist any sexual advances made by the female. Many observers feel the refractory period provides a more realistic evaluation of libido enhancement. On necropsy examinations of the secondary sex organs of the animals treated, i.e., the ventral prostate and seminal vesicles, fail to show any overt, peripheral, somatic effects normally associated with androgen administration, and more particularly associated with the administration of testosterone.

The compounds of the present invention can be administered in various unit dosage forms including tablets or lozenges for purposes of absorption through the buccal mucosa. The active ingredient may be enclosed in hard or soft gelatin capsules, or it may be compressed directly into tablets, or they may be incorporated with other pharmaceutical excipients and inert diluents and used in the form of troches, elixirs, suspensions, syrups, wafers, chewing gum and the like. Such compositions and preparations can contain anywhere from 0.1 milligram to about 3 grams of active compound per dosage unit form. Preferably an amount of active ingredient ranging from 0.1 milligram to 500 milligrams is employed per dosage unit. The tablets, troches, pills and capsules may also contain the following pharmaceutical excipients: a binder such as gum tragacanth, acacia, corn starch or gelatin, a diluent such as dicalcium phosphate; a disintegrating agent such as corn starch, potato starch, alginic acid; a lubricant such as magnesium stearate; a sweetening agent such as sucrose, lactose or saccharin, and flavoring agents such as peppermint, oil of wintergreen or cherry flavoring. Various other materials may also be present as coatings or to otherwise modify the physical form of the dosage unit, as for example, shellac-coated tablets or capsules and sugar-coated tablets. Syrups or elixirs may contain the active ingredients, sucrose as a sweetening agent, methyl and propyl parabens as preservatives, and a suitable dye or flavoring agent.

Parenteral fluid dosage forms or injectable forms including those which can be administered by a jet gun are prepared by utilizing the active ingredient in a sterile liquid vehicle such as water or saline solution. Compositions having the desired clarity, stability and adaptability for parenteral use are obtained by dissolving from about 0.1 milligram to about 3 grams of the active ingredient in a vehicle consisting of a mixture of nonvolatile, liquid polyethylene glycols which are soluble in water and organic liquids and which have molecular weights ranging from about 200 to about 1,500. Such solutions may advantageously contain suspending agents, such as sodium carboxymethylcellulose, methylcellulose, polyvinyl pyrrolidone or polyvinyl alcohol. In the case of injectable forms, they may also contain preservatives in the nature of bactericidal and fungicidal agents, as for example, parabens, benzyl alcohol, phenol or thimerosal. If desired, isotonic agents are included such as various sugar or sodium chloride. Adjuvants include local anesthetics and stabilizing or buffering agents may also be usefully employed.

The active ingredient can also be compressed into pellets or small cylinders and implanted subcutaneously or intramuscularly as depot injections or implants. Implants may employ inert materials such as biodegradable polymers or synthetic silicones, as for example, Silastic, silicone rubber manufactured by the Dow-Corning Corporation. Implantation results in a slow but, nevertheless, predictable rate of absorption from the site of implantation.

The following preparations and examples are illustrative of the preparation of the novel compounds and compositions of the present invention, but are not to be construed as necessarily limiting the scope thereof.

EXAMPLE 1

5α-Bromo-3β,6β-dihydroxyandrostan-17-one 3-acetate

A solution of 3β-hydroxy-5-androsten-17-one acetate in ether is cooled to −5° C. in an ice-methanol bath and a solution of aqueous perchloric acid added followed by the addition of N-bromoacetamide. Stirring at −5° C. is continued for about 2 hours and water added. The ether layer is washed with water until neutral and concentrated to a small volume at room temperature. The product which separates is filtered and crystallized from an acetone-hexane solution to yield 5α-bromo-3β,6β-dihydroxyandrostan-17-one 3-acetate.

Substituting 5-androstene-3β,17β-diol diacetate for the 3β-hydroxy-5-androsten-17-one acetate above results in the preparation of 5α-bromo-androstane-3β,6β,17β-triol 3,17-diacetate.

EXAMPLE 2

5α-Bromo-3β-hydroxy-6β,19-oxidoandrostan-17-one acetate

A stirred suspension of lead tetraacetate and calcium carbonate in cyclohexane is refluxed for approximately 30 minutes and iodine and 5α-bromo-3β,6β-dihydroxyandrostan-17-one 3-acetate is added. The stirred mixture is irradiated with a 600 Watt lamp which maintains the reaction mixture at its reflux temperature. Following the disappearance of the iodine color, the mixture is cooled, filtered and the residue washed with ether. The filtrates are combined and concentrated to one-fifth volume, washed with a 10% sodium thiosulfate solution, followed by a water wash, dried over magnesium sulfate and evaporated under reduced pressure. A semi-solid residue is obtained which is crystallized from an acetone-hexane solution to yield 5α- bromo-3β-hydroxy-6β,19-oxidoandrostan-17-one acetate.

Substituting 5α-bromo-androstane-3β,6β,17β-triol 3,17- diacetate for the 5β-bromo-3β,6β-dihydroxyandrostan-17-one 3-acetate above results in the preparation of 5α- bromo-6β,19-oxidoandrostane-3β,17β-diol diacetate.

EXAMPLE 3

3β,19-Dihydroxy-5-androsten-17-one 3-acetate

Zinc powder is added to a solution of 5α-bromo-3β-hydroxy-6β,19-oxidoandrostan-17-one acetate in ethanol and the mixture heated at its reflux temperature with stirring for about 3 hours. The suspension is filtered and the zinc cake washed with hot ethanol. Removal of the solvent from the combined filtrates leaves a residue which when crystallized from an acetone-hexane solution yields 3β,19-dihydroxy-5-androsten-17-one 3-acetate.

Substituting 5α-bromo-6β,19-oxidoandrostane-3β,17β-diol diacetate for the 5α-bromo-3β-hydroxy-6β,19-oxidoandrostan-17-one acetate above results in the preparation of 5-androstene-3β,17β,19-triol 3,17-diacetate.

EXAMPLE 4

3β,19-Dihydroxy-5-androsten-17-one diacetate

Zinc powder is added to a solution of 5α-bromo-3β-hydroxy-6β,19-oxidoandrostan-17-one acetate in acetic acid and the mixture is heated at its reflux temperature with stirring for 3 hours. The suspension is filtered and the zinc cake washed with hot acetic acid. The combined filtrates are poured onto ice water with vigorous stirring. The solid which forms is collected by vacuum filtration and washed with water. Crystallization from acetone yields 3β,19-dihydroxy-5-androsten-17-one diacetate.

Substituting 5α-bromo-6β,19-oxidoandrostane-3β,17β-diol diacetate for the 5α-bromo-3β-hydroxy-6β,19-oxidoandrostan-17-one acetate above results in the preparation of 5-androstene-3β,17β,19-triol triacetate.

EXAMPLE 5

3β,19-Dihydroxy-5-androsten-17-one

A solution of 3β,19-dihydroxy-5-androsten-17-one 3-acetate and a solution of 5% aqueous sodium carbonate in methanol is heated at its reflux temperature for two hours. The solvent is removed under reduced pressure and ether added. The ethereal solution is washed with water, dried over magnesium sulfate and evaporated in vacuo. The residue is crystallized from an acetone-hexane solution to yield 3β,19-dihydroxy-5-androsten-17-one.

Substituting 5-androstene-3β,17β,19-triol triacetate for the 3β,19-dihydroxy-5-androsten-17-one 3-acetate above results in the preparation of 5-androstene-3β,17β,19-triol.

EXAMPLE 6

3β,19-Dihydroxy-5-androsten-17-one 19-acetate

To a solution of 3β,19-dihydroxy-5-androsten-17-one diacetate in methanol is added one equivalent of an aqueous 2% solution of potassium hydrogen carbonate. The mixture is heated at its reflux temperature approximately 2 hours. The solution is evaporated to a small volume under reduced pressure and ether added. The ethereal solution is thoroughly washed with water, dried over magnesium sulfate and evaporated in vacuo. The residue is dissolved in a minimum volume of benzene and chromatographed on a column of silica gel. Elution with a benzeneethylacetate soliution results in an eluate from which pure 3β,19-dihydroxy-5-androsten-17-one 19-acetate is obtained.

EXAMPLE 7

3β,19-Dihydroxy-5α-androstan-17-one diacetate

A solution of 3β,19-dihydroxyandrost-5-en-17-one diacetate in methanol is hydrogenated with a 10% Palladium-on-charcoal catalyst at atmospheric pressure for 8 hours. The catalyst is removed by filtration and the filtrate concentrated to a small volume, cooled, and filtered to yield the desired 3β,19-dihydroxy-5α-androstan-17-one diacetate. Recrystallization from hexane results in pure material.

Substituting 5-androstene-3β,17β,19-triol 3,17-diacetate, 5-androstene-3β,17β,19-triol triacetate, 3β,19-dihydroxy-5-androsten-17-one 3-acetate, 3β,19-dihydroxy-5-androsten-17-one, 5-androstene-3β,17β,19-triol and 3β,19-dihydroxy-5-androsten-17-one 19-acetate for the 3β,19-dihydroxyandrost-5-en-17-one diacetate above results in the preparation of 5α-androstane-3β,17β,19-triol 3,17-diacetate, 5α-androstane-3β,17β,19-triol triacetate, 3β,19-dihydroxy-5α-androstan-17-one 3-acetate, 3β,19-dihydroxy-5α-androstan-17-one, 5α-androstane-3β,17β,19-triol and 3β,19-dihydroxy-5α-androstan-17-one 19-acetate, respectively.

EXAMPLE 8

5α-Androstane-3β,17β,19-triol 3,19-diacetate

A tetrahydrofuran solution of 3β,19-dihydroxy-5α-androstan-17-one diacetate is added to lithium tri-t-butoxyaluminum hydride in tetrahydrofuran and the resultant solution stirred overnight at room temperature. Aqueous sodium potassium tartrate is added with stirring until a readily filterable precipitate forms. The filtrate is concentrated under reduced pressure and diluted with ether. The resulting solution is washed with water, dried over magnesium sulfate and the ether removed under vacuum. The residual 5α-androstane-3β,17β,19-triol 3,19-diacetate is crystallized from an acetone-hexane solution.

EXAMPLE 9

17α-Methyl-5α-androstane-3β,17β,19-triol

To a solution of 3β,19-dihydroxy-5α-androstan-17-one diacetate in ether is added 10 equivalents of ethereal methyllithium. The resulting mixture is stirred at room temperature for about 18 hours. The reaction mixture is decomposed with an aqueous ammonium chloride solution and the ether layer washed with water, dried over magnesium sulfate and concentrated under vacuum. Crystallization of the residue from acetone-hexane yields pure 17α-methyl-5α-androstane-3β,17β,19-triol.

EXAMPLE 10

17α-Ethinyl-5α-androstane-3β,17β,19-triol

Dry acetylene is bubbled through dry ether for 30 minutes with stirring. Potassium t-amylate in t-amyl alcohol and 3β,19-dihydroxy-5α-androstan-17-one in ether are added dropwise to this solution. Stirring is continued at room temperature for about 5 hours while acetylene is bubbled through the reaction mixture. The reaction mixture is then acidified with aqueous ammonium chloride containing a drop of hydrochloric acid and thoroughly extracted with ether. The combined ether extracts are washed with water, dried over magnesium sulfate and evaporated under reduced pressure. The residue is crystallized from an acetonehexane solution to yield 17α-ethinyl-5α-androstane-3β,17β,19-triol.

EXAMPLE 11

17α-Vinyl-5α-androstane-3β,17β,19-triol

A solution of vinyllithium in tetrahydrofuran is added dropwise to a solution of 3β,19-dihydroxy-5α-androstan-17-one in tetrahydrofuran. The resulting mixture is stirred at room temperature for about 18 hours. The reaction mixture is decomposed with aqueous ammonium chloride and the ether layer washed well with water, dried over magnesium sulfate and concentrated under vacuum. Crystallization of the residue from an acetone-hexane solution yields 17α-vinyl-5α-androstane-3β,17β,19-triol.

EXAMPLE 12

5α-Androstane-3,17,19-trione

To a solution of 3β,19-dihydroxy-5α-androstan-17-one in acetone chilled to 10° C. is added exactly two equivalents of Jones reagent. After standing for 15 minutes the upper acetone layer is poured into water with vigorous stirring. The solid which forms is filtered, air dried and crystallized from hexane to yield 5α-androstane-3,17,19-trione.

Substituting 17α-methyl-5α-androstane-3β,17β,19-triol, 17α-ethinyl-5α-androstane-3β,17β,19-triol and 17α-vinyl-5α-androstane-3β,17β,19-triol for the 3β,19-dihydroxy-5α-androstan-17-one above results in the preparation of 17β-hydroxy-17α-methyl-5α-androstane-3,19-dione, 17α-ethinyl-17β-hydroxy-5α-androstane-3,19-dione and 17β-hydroxy-17α-vinyl-5α-androstane-3,19-dione, respectively.

EXAMPLE 13

19-Hydroxy-5α-androstane-3,17-dione acetate

To a solution of 3β,19-dihydroxy-5α-androstane-17-one 19-acetate in acetone chilled to 10° C. is added one equivalent of Jones reagent. After standing for 30 minutes the upper acetone layer is poured onto water with vigorous stirring. The soild which forms is filtered, air dried and crystallized from hexane to yield 19-hydroxy-5α-androstane-3,17-dione acetate.

Substituting 5α-androstane-3β,17β,19-triol 3,17-diacetate for the 3β,19-dihydroxy-5α-androstane-17-one 19-acetate above results in the preparation of 3β,17β-dihydroxy-5α-androstan-19-one diacetate.

EXAMPLE 14

5α-Androstane-3α,17β,19-triol

A 1 M solution of lithium tri-sec-butylborohydride in tetrahydrofuran under nitrogen is cooled in a dry ice-acetone bath to −78° C. and 19-hydroxy-5α-androstane-3,17-dione acetate is slowly added. The reaction mixture is stirred for 2 hours at this temperature, warmed to 0° C. and stirring continued for an additional two hours. The reaction mixture is decomposed by the addition of 3 N sodium hydroxide solution followed by a 30% hydrogen peroxide solution. Solid potassium carbonate is added to this mixture and the tetrahydrofuran decanted therefrom. The solid residue is washed with fresh tetrahydrofuran and the combined tetrahydrofuran solutions are dried over anhydrous sodium sulfate, filtered, and evaporated to dryness. The residue is crystallized from acetone to yield 5α-androstane-3α,17β,19-triol.

EXAMPLE 15

17β,19-Dihydroxy-1,4-androstadien-3-one dipropionate

17β,19-Dihydroxy-4-androsten-3-one dipropionate and dichlorodicyanobenzoquinone are refluxed in anhydrous dioxane for about 48 hours. The mixture is cooled and filtered. The filtrate is concentrated under vacuum, methylenechloride is added and the mixture filtered. The filtrate is washed well with water, dried over sodium sulfate and the solvent removed. Chromatography of the residue on silica gel and eluting with methylenechloride yields an eluate. Removal of the solvent results in a solid which is crystallized from an acetone-hexane solution to yield the desired 17β,19-dihydroxy-1,4-androstadien-3-one dipropionate.

Substituting 17β,19-dihydroxy-17α-methyl-4-androsten-3-one dipropionate, 19-hydroxy-4-androstene-3,17-dione propionate, 17β,19-dihydroxy-7α-methyl-4-androsten-3-one dipropionate and 17β,19-dihydroxy-6α,17α-dimethyl-4-androsten-3-one dipropionate for the 17β,19-dihydroxy-4-androsten-3-one dipropionate above results in the preparation of 17β,19-dihydroxy-17α-methyl-1,4-androstadien-3-one dipropionate, 19-hydroxy-1,4-androstadiene-3,17-dione propionate, 17β,19-dihydroxy-7α-methyl-1,4-androstadien-3-one dipropionate and 17β,19-dihydroxy-6α,17α-dimethyl-1,4-androstadiene-3-one dipropionate.

EXAMPLE 16

17β,19-Dihydroxy-1α-methyl-4-androsten-3-one dipropionate

A solution of lithium dimethylcopper is prepared under nitrogen by the addition of 1.6 M ethereal methyllithium to an ether slurry of cuprous iodide at 0° C. The solution is stirred at 0° for 20 minutes, a solution of 17β,19-dihydroxy-1,4-androstadien-3-one dipropionate in anhydrous tetrahydrofuran is slowly added and stirring continued for one half hour. The mixture is poured onto a saturated aqueous ammonium chloride solution, benzene is added and the resulting mixture filtered through diatomaceous earth. The organic layer is washed with an aqueous ammonium chloride solution, washed with water, dried over magnesium sulfate and evaporated to dryness. The residue which remains is passed through a silica gel column and eluted with benzene. The eluate is concentrated to dryness. Recrystallization from hexane yields 17β,19-dihydroxy-1α-methyl-4-androsten-3-one dipropionate.

Substituting 17β,19-dihydroxy-17α-methyl-1,4-androstadien-3-one dipropionate, 19-hydroxy-1,4-androstadiene-3, 17-dione propionate, 17β,19-dihydroxy-7α-methyl-1,4-androstadien-3-one dipropionate and 17β,19-dihydroxy-6α, 17α-dimethyl-1,4-androstadien-3-one dipropionate for the 17β,19-dihydroxy-1,4-androstadien-3-one dipropionate above results in the preparation of 17β,19-dihydroxy-1α,17α-dimethyl-4-androsten-3-one dipropionate, 19-hydroxy-1α-methyl-4-androstene-3,17-dione propionate, 17β,19-dihydroxy-1α,7α-dimethyl-androst-4-en-3-one dipropionate and 17β,19-dihydroxy-1α,6α,17α-trimethyl-4-androsten-3-one dipropionate, respectively.

EXAMPLE 17

3-Ethoxy-1α-methyl-3,5-androstadiene-17β,19-diol dipropionate

A solution of 17β,19-dihydroxy-1α-methyl-4-androsten3-one dipropionate, triethylorthoformate, p-toluenesulfonic acid and ethanol in tetrahydrofuran is stirred at room temperature for about 2 hours. The reaction mixture is poured onto ice water containing a few drops of pyridine and stirred well. The solid which forms is filtered and crystallized from ethanol to yield pure 3-ethoxy-1α-methyl-3,5-androstadiene-17β,19-diol dipropionate.

Substituting 17β,19-dihydroxy-1α,17α-dimethyl-4-androsten-3-one dipropionate, 19-hydroxy-1α-methyl-4-androstene-3,17-dione propionate, 17β,19-dihydroxy-1α,7α-dimethyl-4-androsten-3-one dipropionate and 17β,19-dihydroxy-1α,6α,17α-trimethyl-4-androsten-3-one dipropionate for the 17β,19-dihydroxy-1α-methyl-4-androsten-3-one dipropionate above results in the preparation of 3-ethoxy-1α,17α-dimethyl-3,5-androstadien-17β,19-diol dipropionate, 3-ethoxy-19-hydroxy-1α-methyl-3,5-androstadien-17-one propionate, 3-ethoxy-1α,7α-dimethyl-3,5-androstadien-17β,19-diol dipropionate and 3-ethoxy-1α,6α,17α-trimethyl-3,5-androstadien-17β,19-diol propionate, respectively.

EXAMPLE 18

17β,19-Dihydroxy-1α-methyl-5α-androstan-3-one dipropionate

A solution of 3-ethoxy-1α-methyl-3,5-androstadien-17β,19-diol dipropionate in ethyl acetate is hydrogenated with platinum oxide at atmospheric pressure. The solution is filtered and the solvent removed under reduced pressure. The residue is taken up in aqueous methanol containing a drop of hydrochloric acid and stirred for 20 minutes at room temperature. The methanol is removed and ether added. The ether extract is washed with water, dried over magnesium sulfate and concentrated. Crystallization of the residue from an acetone-hexane solution yields 17β,19-dihydroxy-1α-methyl-5α-androstan-3-one dipropionate.

Substituting 3-ethoxy-1α,17α-dimethyl-3,5-androstadien-17β,19-diol dipropionate, 3-ethoxy-1α,7α-dimethyl-3,5-androstadien-17β,19-diol dipropionate, 3-ethoxy-19-hydroxy-1α-methyl-3,5-androstadien-17-one propionate and 3-ethoxy-1α,6α,17α-trimethyl-3,5-androstadien-17β,19-diol for the 3-ethoxy-1α-methyl-3,5-androstadien-17β,19-diol dipropionate above results in the preparation of 17β,19-dihydroxy-1α,17α-dimethyl-5α-androstan-3-one dipropionate, 17β,19-dihydroxy-1α,7α-dimethyl-5α-androstan-3-one dipropionate, 19-hydroxy-1α-methyl-5α-androstane-3,17-dione propionate and 17β,19-dihydroxy-1α,6α,17α-trimethyl-5α-androstane-3-one dipropionate, respectively.

EXAMPLE 19

17β,19-Dihydroxy-1α-methyl-5α-androstan-3-one

A solution of 17β,19-dihydroxy-1α-methyl-5α-androstan-3-one dipropionate in methanol is refluxed for two hours with aqueous sodium carbonate. The methanol is removed under vacuum and water added to the residue. Crystallization of the solid residue from an acetone-hexane solution yields pure 17β,19-dihydroxy-1α-methyl-5α-androstan-3-one.

Substituting 17β,19-dihydroxy-1α,17α-dimethyl-5α-androstan-3-one dipropionate, 17β,19-dihydroxy-1α,7α-dimethyl-5α-androstan-3-one dipropionate, 19-hydroxy-1α-methyl-5α-androstane-3,17-dione propionate and 17β,19-dihydroxy-1α,6α,17α-trimethyl-5α-androstan-3-one dipropionate for the 17β,19-dihydroxy-1α-methyl-5α-androstan-3-one dipropionate above results in the preparation of 17β,19-dihydroxy-1α,17α-dimethyl-5α-androstan-3-one, 17β,19-dihydroxy-1α,7α-dimethyl-5α-androstan-3-one, 19-hydroxy-1α-methyl-5α-androstane-3,17-dione and 17β,19-dihydroxy-1α,6α,17α-trimethyl-5α-androstan-3-one, respectively.

EXAMPLE 20

1α-Methyl-17β,19-(di(trimethylsiloxy)-5α-androstan-3-one

A mixture of 17β,19-dihydroxy-1α-methyl-5α-androstan-3-one, trimethylchlorosilane and pyridine in benzene is heated to its reflux temperature for a period of about 14 hours. The reaction mixture is vacuum filtered, the organic layer is washed with water, dried over magnesium sulfate and concentrated in vacuum. Crystallization of the residue from hexane yields 1α-methyl-17β,19-di(trimethylsiloxy)-5α-androstan-3-one.

Substituting 3β,19-dihydroxy-5α-androstan-17-one, 5α-androstane-3β,17β,19-triol 3,17-diacetate, and 5α-androstane-3β,17β,19-triol 3,19-diacetate for the 17β,19-dihydroxy-1α-methyl-5α-androstan-3-one above results in the preparation of 3β,19-di(trimethylsiloxy)-5α-androstan-17-one, 19-trimethylsiloxy-5α-androstane-3β,17β-diol diacetate and 17-trimethylsiloxy-5α-androstane-3β,19-diol diacetate, respectively.

EXAMPLE 21

1α,7α-Dimethyl-17β,19-di(triphenylsiloxy)-5α-androstan-3-one

A solution of 17β,19-dihydroxy-1α,7α-dimethyl-5α-androstan-3-one, triphenylchlorosilane and pyridine in benzene is heated at its reflux temperature for about 24 hours. The reaction mixture is filtered, washed with water, dried over magnesium sulfate and concentrated in vacuo. Pure 1α,7α-dimethyl-17β,19-di(triphenylsiloxy)-5α-androstan-3-one is obtained on crystallization of the residue from hexane.

Substituting 5α-androstane-3β,17β,19-triol, 3β,19-dihydroxy-5α-androstan-17-one 19-acetate and 3β,19-dihydroxy-5α-androstan-17-one 3-acetate for the 17β,19-dihydroxy-1α,7α-dimethyl-5α-androstan-3-one above results in the preparation of 3β,17β,19-tri(triphenylsiloxy)-5α-androstane, 19-hydroxy-3β-triphenylsiloxy-5α-androstan-17-one acetate and 3-hydroxy-19-triphenylsiloxy-5α-androstan-17-one acetate, respectively.

EXAMPLE 22

19-Trimethylsiloxy-5α-androstane-3β,19β-diol

A solution of 19-trimethylsiloxy-5α-androstane-3β,17β-diol diacetate in ether is added to a lithium aluminum hydride suspension in ether. After refluxing for one hour, the excess hydride is destroyed with water. The ether solution is separated, dried over sodium sulfate and concentrated under vacuum. The residue which remains is crystallized from methanol to yield 19-trimethylsiloxy-5α-androstane-3β,17β-diol.

Substituting 17β-trimethylsiloxy-5α-androstane-3β,19-diol diacetate, 19-hydroxy-3β-triphenylsiloxy-5α-androstan-17-one acetate and 1α-methyl-17β,19-di(trimethylsiloxy)-5α-androstan-3-one for the 19-trimethylsiloxy-5α-androstane-3β,17β-diol diacetate above results in the preparation of 17β-trimethylsiloxy-5α-androstane-3β,19-diol, 3β-triphenylsiloxy-5α-androstane-17β,19-diol and 1α-methyl-17β,19-di(trimethylsiloxy)-5α-androstan-3β-ol.

EXAMPLE 23

19-Trimethylsiloxy-5α-androstane-3,17-dione

19-Trimethylsiloxy-5α-androstane-3β,17β-diol is dissolved in acetone and chilled to 10° C. Jones reagent is added with stirring over a period of 5 minutes and the mixture left standing for an additional 20 minutes. The acetone layer is poured onto water with vigorous stirring. The solid which forms is collected by filtration, air dried and crystallized from an acetone-hexane solution to yield 19-trimethylsiloxy-5α-androstane-3,17-dione.

Substituting 17β-trimethylsiloxy-5α-androstane-3β,19-diol and 3β-triphenylsiloxy-5α-androstane-17,19-diol for the 19-trimethylsiloxy-5α-androstane-3β,17β-diol above results in the preparation of 17β-trimethylsiloxy-5α-androstane-3,19-dione and 3β-triphenylsiloxy-5α-androstane-17,19-dione.

EXAMPLE 24

1β,2β-Methylene-4-androstene-3,17-dione

To a solution of potassium t-butoxide in dimethylsulfoxide at 25° under nitrogen is added 1,4-androstadiene-3,17-dione in dimethylsulfoxide with stirring. After 15 minutes the mixture is poured onto cold aqueous ammonium chloride. The solid which forms is rapidly filtered, washed well with water and dissolved in ether. The ether solution is washed with water, dried over sodium sulfate and evaporated at room temperature to yield 1,5-androstadiene-3,17-dione.

A tetrahydrofuran solution of 1,5-androstadiene-3,17-dione is added to a solution of lithium tri-t-butoxyaluminum hydride in tetrahydrofuran under nitrogen. After stirring overnight at room temperature, an aqueous solution of potassium sodium tartrate is added with stirring to form a readily filterable white solid. The reaction mixture is filtered and the filtrate dried over magnesium sulfate. The solvent is removed and the residue recrystallized from acetone to yield 1,5-androstadiene-3β,17β-diol.

To a stirred solution consisting of 1,5-androstadiene-3β,17β-diol in a mixture of dry ether and glyme is added zinc-copper couple and methylene iodide. This mixture is refluxed for approximately 4 hours, cooled to room temperature, diluted with ether and filtered. The filtrate is washed with aqueous sodium chloride, water and dried over anhydrous magnesium sulfate. The ether is removed under reduced pressure and the residue is crystallized from an acetone-hexane solution to yield 1β,2β-methylene-5-androstene-3β,17β-diol.

1β,2β-Methylene-5-androstene-3β,17β-diol is dissolved in acetone and Jones reagent is added until a persistent yellow orange color appears. After stirring at room temperature for 10 minutes the mixture is poured onto icewater. The precipitate is collected by filtration and dissolved in a solution of sodium methoxide in methanol. Stirring is continued for about 30 minutes at room temperature, the methanol is removed and the residue triturated with water. The solid is filtered and crystallized from acetone to yield 1β,2β-methylene-4-androstene-3,17-dione.

Substituting 7α-methyl-1,4-androstadiene-3,17-dione and 6α-methyl-1,4-androstadiene-3,17-dione for the 1,4-androstadiene-3,17-dione above results in the preparation of 7α-methyl-1β,2β-methylene-4-androstene-3,17-dione and 6α-methyl-1β,2β-methylene-4-androstene-3,17-dione.

EXAMPLE 25

1β-Methyl-4-androstene-3,17-dione

A mixture of 1β,2β-methylene-4-androstene-3,17-dione, zinc powder, and acetic acid is refluxed for one hour. Benzene is added and the suspension filtered. The filtrate is taken to dryness under vacuum. The residue which remains is chromatographed on silica gel and eluted with methylenechloride. Recrystallization of the residue obtained from the eluate from an acetone-hexane solution yields 1β-methyl-4-androstene-3,17-dione.

Substituting 7α-methyl-1β,2β-methylene-4-androstene-3,17-dione and 6α-methyl-1β,2β-methylene-4-androstene-3,17-dione for the 1β,2β-methylene-4-androstene-3,17-dione above results in the preparation of 1β,7β-dimethyl-4-androstene-3,17-dione and 1β,6α-dimethyl-4-androstene-3,17-dione.

EXAMPLE 26

1β-Methyl-5-androstene-3β,17β-diol diacetate

To a solution of potassium t-butoxide in dimethylsulfoxide under nitrogen at 25° C. is added 1β-methyl-4-androstene-3,17-dione in dimethylsulfoxide with stirring. After 15 minutes the mixture is poured onto a cold aqueous ammonium chloride solution. The solid which forms is rapidly filtered, washed well with water and redissolved in ether. The ether solution is washed with water and dried over sodium sulfate. The ether is removed at room temperature to yield 1β-methyl-5-androstene-3,17-dione.

A tetrahydrofuran solution of 1β-methyl-5-androstene-3,17-dione is added under nitrogen to a solution of lithium tri-t-butoxyaluminum hydride in tetrahydrofuran. After stirring at room temperature for about 18 hours, an aqueous solution of potassium sodium tartrate is added with stirring to form a readily filterable white solid. The reaction mixture is filtered, the filtrate dried over magnesium sulfate and the solvent removed. The residue which remains is crystallized from an acetone-hexane solution to yield 1β-methyl-5-androstene-3β,17β-diol.

The 1β-methyl-5-androstene-3β,17β-diol so formed is dissolved in acetic anhydride and pyridine and kept at room temperature for approximately 20 hours. The solvent is removed under vacuum and the residue recrystallized from a solution of hexane to yield 1β-methyl-5-androstene-3β,17β-diol diacetate.

Substituting 1α,7β-dimethyl-4-androstene-3,17-dione and 1β,6α-dimethyl-4-androstene-3,17-dione for the 1β-methyl-4-androstene-3,17-dione above results in the preparation of 1,62, 7αdimethyl-5-androstene-3β,17β-diol diacetate and 1β,6-dimethyl-5-androstene-3β,17β-diol diacetate, respectively.

EXAMPLE 27

5α-Bromo-1β-methylandrostene-3β,6β,17-triol 3,17-diacetate

A solution of 1β-methyl-5-androstene-3β,17β-diol diacetate in ether is cooled to −5° C. in an ice-methanol bath and a solution of aqueous perchloric acid added followed by the addition of N-bromoacetamide. Stirring at −5° C. is continued for approximately two hours followed by the addition of water. The ether layer is washed with water until neutral and concentrated to a small volume at room temperature. The product which remains is filtered and crystallized from an acetone-hexane solution to yield 5α-bromo-1β-methylandrostene-3β,6β, 17β-triol, 3,17-diacetate.

Substituting 1β,7α-dimethyl-5-androstene-3β,17β-diol diacetate and 1β,6-dimethyl-5-androstene-3β,17β-diol diacetate for the 1β-methyl-5-androstene-3β,17β-diol diacetate above results in the preparation of 5α-bromo-1β,7α-dimethylandrostene-3β,6β,17β-triol 3,17-diacetate and 5α-bromo-1β,6α-dimethylandrostene-3β,6β,17β-triol 3,17-diacetate, respectively.

EXAMPLE 28

5α-Bromo-1β-methyl-6β,19-oxidoandrostane-3β,17β-diol diacetate

A stirred suspension of lead tetraacetate and calcium carbonate in cyclohexane is refluxed for 30 minutes followed by the addition of iodine and 5α-bromo-1β-methylandrostane-3β,6β,17β-triol 3,17-diacetate. The stirred mixture is irradiated with a 600 Watt lamp which maintains the mixture at reflux. After the iodine color has disappeared the mixture is cooled, filtered and the residue washed with ether. The filtrates are combined, concentrated to one/fifth volume, washed with a 10% sodium thiosulfate solution, washed with water, dried over magnesium sulfate and evaporated under reduced pressure to yield a semi-solid residue. This residue is crystallized from an acetone-hexane solution to yield 5α-bromo-1β-methyl-6β,19-oxidoandrostane-3β,17β-diol diacetate.

Substituting 5α-bromo-1β,7α-dimethylandrostane-3β,6β,17β-triol 3,17-diacetate and 5α-bromo-1β,6α-dimethylandrostane-3β,6β,17β-triol 3,17-diacetate for the 5α-bromo-1β-methylandrostane-3β,6β,17β-triol 3,17-diacetate above results in the preparation of 5α-bromo-1β,7α-dimethyl-6β,19-oxidoandrostane-3β,17β-diol diacetate and 5α-bromo-1,62 ,6α-dimethyl-6β,19-oxidoandrostane-3β,17β-diol diacetate, respectively.

EXAMPLE 29

1β-Methyl-5-androstene-3β,17β,19-triol 3,17-diacetate

Zinc powder is added to a solution of 5α-bromo-1β-methyl-6β,19-oxidoandrostane-3β,17β-diol diacetate in ethanol and the mixture heated at its reflux temperature with stirring for approximately 3 hours. The suspension is filtered and the zinc cake washed with hot ethanol. Removal of the solvent from the combined filtrates results in a residue which is crystallized from an acetone-hexane solution to yield 1β-methyl-5-androstene-3β,17β,19-triol 3,17-diacetate.

Substituting 5α-bromo-1β,7α-dimethyl-6β,19-oxidoandrostane-3β,17β-diol diacetate and 5α-bromo-1β,6α-dimethyl-6β,19-oxidoandrostane-3β,17β-diol diacetate for the 5α-bromo-1β-methyl-6β,19-oxidoandrostane-3β,17β-diol diacetate above results in the preparation of 1,62 ,7α-dimethyl-5-androstene-3β,17β,19-triol 3,17-diacetate and 1β,6-dimethyl-5-androstene-3β,17β,19-triol 3∫-diacetate, respectively.

EXAMPLE 30

1β-Methyl-5-androstene-3β,17β,19-triol triacetate

Zinc powder is added to a solution of 5α-bromo-1β-methyl-6β,19-oxidoandrostane-3β,17β-diol diacetate in acetic acid and the mixture heated at its reflux temperature with stirring for about 3 hours. The suspension is filtered and the zinc cake washed with hot acetic acid. The combined filtrates are poured onto ice water with vigorous stirring. The solid which forms is collected by vacuum filtration and washed with water. Crystallization of this material from an acetone-hexane solution yields 1β-methyl-5-androstene-3β,17β,19-triol triacetate.

Substituting 5α-bromo-1β,7α-dimethyl-6β,19-oxidoandrostane-3β,17β-diol diacetate and 5α-bromo-1β,6α-dimethyl-6β,19-oxidoandrostane-3β,17β-diol diacetate for the 5α-bromo-1β,19-oxidoandrostane-3β,17β-diol diacetate above results in the preparation of 1β,7α-dimethyl-5-androstene-3β,17β,19-triol triacetate and 1β,6-dimethyl-5-androstene-3β,17β,19-triol triacetate, respectively.

EXAMPLE 31

1β-Methyl-5α-androstane-3β,17β,19-triol 3,17-diacetate

A solution of 1β-methyl-5-androstene-3β,17β,19-triol 3,17-diacetate in methanol is hydrogenated with a 10% palladium-on-carbon catalyst at atmospheric pressure for about 8 hours. The catalyst is removed by filtration, the filtrate is concentrated to a small volume, cooled and filtered. The residue is crystallized from a solution of hexane to yield 1β-methyl-5α-androstane-3β,17β,19-triol 3,17-diacetate.

Substituting 1β,7α-dimethyl-5-androstene-3β,17β,19-triol 3,17-diacetate, 1β-methyl-5-androstene-3β,17β,19-triol triacetate and 1β,6-dimethyl-5-androstene-3β,17β,19-triol triacetate for the 1β-methyl-5-androstene-3β,17β,19-triol 3,17-diacetate above results in the preparation of 1β,7α-dimethyl-5α-androstane-3β,17β,19-triol 3,17-diacetate, 1β-methyl-5α-androstane-3β,17β,19-triol triacetate and 1β,6β-dimethyl-5α-androstane-3β,17β,19-triol triacetate, respectively.

EXAMPLE 32

1β-Methyl-19-(2′-tetrahydropyranyloxy)-5α-androstan-3β,17β-diol diacetate

To a stirred solution of 1β-methyl-5α-androstane-3β,17β,19-triol 3,17-diacetate and p-toluenesulfonic acid in anhydrous dioxane is added dihydropyran slowly. After 15 minutes methanolic ammonia is added until the solution becomes slightly basic. The solvent is removed under vacuum and the residual oil is dissolved in methylenechloride. The methylenechloride solution is extracted with an aqueous sodium bicarbonate solution, dried over sodium sulfate and concentrated under vacuum. The residue which remains is crystallized from a solution of hexane to yield 1β-methyl-19-(2′-tetrahydropyranyloxy)-5α-androstan-3β,17β-diol diacetate.

Substituting 5α-androstane-3β,17β,19-triol 3,17-diacetate and 19-hydroxy-5α-androstane-3,17-dione for the 1β-methyl-5α-androstane-3β,17β,19-triol 3,17-diacetate above results in the preparation of 19-(2′-tetrahydropyranyloxy)-5α-androstan-3β,17β-diol diacetate and 19-(2′-tetrahydropyranyloxy)-5α-androstan-3,17-dione, respectively.

EXAMPLE 33

1β-Methyl-19-(2′-tetrahydropyranyloxy)-5α-androstane-3β,17β-diol

A solution of 1β-methyl-19-(2′-tetrahydropyranyloxy)-5α-androstane-3β,17β-diol diacetate and sodium carbonate in aqueous methanol is refluxed for about 2 hours. This mixture is concentrated to approximately half volume and poured onto water with stirring. The oil which forms is extracted into ether. The ether extract is washed with water, dried over sodium sulfate and evaporated to dryness. Crystallization of the residue from an acetone-hexane solution yields 1β-methyl-19-(2′-tetrahydropyranyloxy)-5α-androstane-3β,17β-diol.

Substituting 19-(2′-tetrahydropyranyloxy)-5α-androstane-3β,17β-diol diacetate for the 1β-methyl-19-(2′-tetrahydropyranyloxy)-5α-androstane-3β,17β-diol diacetate above results in the preparation of 19-(2′-tetrahydropyranyloxy)-5α-androstane-3β,17β-diol.

EXAMPLE 34

3β,17β-Dihydroxy-1β-methyl-5α-androstan-19-one

One equivalent of Jones reagent is added dropwise to a stirred solution of 1β-methyl-5α-androstane-3β,17β,19-triol 3,17-diacetate in acetone chilled to 0° C. After 15 minutes at 0° C., the acetone layer is poured onto ice water. The solid which forms is filtered and crystallized from an ether-hexane solution to yield 3β,17β-dihydroxy-1β-methyl-5α-androstan-19-one diacetate. This material is dissolved in aqueous methanol containing sodium carbonate and the solution heated at its reflux temperature for about 4 hours. The cooled solution is poured onto water and filtered. The solid which forms is collected and is crystallized from an ether-hexane solution to yield 3β,17β-dihydroxy-1β-methyl-5α-androstan-19-one.

Substituting 5α-androstane-3β,17β,19-triol 3,17-diacetate for the 1β-methyl-5α-androstane-3β,17β,19-triol 3,17-diacetate above results in the preparation of 3β,17β-dihydroxy-5α-androstan-19-one.

EXAMPLE 35

1β-Methyl-3β,17β-di(2′-tetrahydropyranyloxy)-5α-androstan-19-one.

To a stirred solution of 3β,17β-dihydroxy-1β-methyl-5α-androstan-19-one and p-toluenesulfonic acid in anhydrous dioxane is added dihydropyran over a 10 minute period. After an additional 10 minutes, methanolic ammonia is added until the solution becomes slightly basic. The volatile solvents are removed under vacuum and the residual oil is dissolved in ether. The ether solution is extracted with aqueous sodium bicarbonate, dried over sodium sulfate, and concentrated to dryness. Crystallization of the residual gum from a pentane solution yields 1β-methyl-3β,17β-di(2′-tetrahydropyranyloxy)-5α-androstan-19-one.

Substituting 3β,17β-dihydroxy-5α-androstan-19-one for the 3β,17β-dihydroxy-1β-methyl-5α-androstan-19-one above results in the preparation of 3β17β-di(2′-tetrahydropyranyloxy)-5α-androstan-19-one.

EXAMPLE 36

17β,19-Dihydroxy-4,6α,17α-trimethyl-4-androsten-3one

A mixture of 17β,19-dihydroxy-6α,17α-dimethyl-4-androsten-3-one, thiophenol, 40% aqueous formaldehyde, triethylamine and ethanol is heated at the reflux temperature for a period of about 48 hours. The cooled solution is poured into an aqueous sodium hydroxide solution and the product isolated by ether extraction. The ether extract is washed with water and dried over magnesium sulfate. The residue which remains after evaporation of the ether is triturated with hexane to remove any condensation product derived from the thiophenol and formaldehyde. The 17β,19-dihydroxy-6α-methyl-4-phenylthiomethyl-4-androsten-3-one so obtained is desulfurized by dissolving the compound in acetone and adding this solution to a suspension of Raney Nickel in refluxing acetone. The mixture is heated at its reflux temperature while stirring for about 5 hours. The hot solution is filtered and the nickel residue washed first with boiling ethanol and then with water. The combined filtrates are concentrated under vacuum and the product separated as a crude solid. Recrystallization of this material from an acetone-hexane solution yields 17β,19-dihydroxy-4,6α,17α-trimethyl-4-androsten-3-one.

EXAMPLE 37

17β-Hydroxy-4,6α,17α-trimethyl-4-androstene-3,19-dione

17β,19-Dihydroxy-4,6α,17α-trimethyl-4-androsten-3-one is added to a mixture of dimethylsulfoxide, benzene, pyridine, trifluoroacetic acid and N,N′-dicyclohexylcarbodiimide and stirred at room temperature for about 12 hours. Ethylacetate is added and the reaction mixture filtered of dicyclohexylurea. The filtrate is washed with water, dried over magnesium sulfate and concentrated under vacuum. Crystallization of the residue from an ether solution yields 17β-hydroxy-4,6α,17α-trimethyl-4-androstene-3,19-dione.

EXAMPLE 38

17β-Hydroxy-4,6α,17α-trimethyl-4-androstene-3,19-dione acetate

17β-Hydroxy-4,6α,17α-trimethyl-4-androstene-3,19-dione, pyridine and acetic anhydride are stirred for about 48 hours at room temperature. The reaction mixture is poured onto ice water. The soild so obtained is removed by filtration and crystallized from an ether-hexane solution to yield 17β-hydroxy-4,6α,17α-trimethyl-4-androstene-3,19-dione acetate.

EXAMPLE 39

4,6α,17α-Trimethyl-17β,19-di(2′-tetrahydropyranyloxy)-4-androsten-3-one

Dihydropyran is slowly added to a solution of 17β,19-dihydroxy-4,6α,17αtrimethyl-4-androsten-3-one and p-toluenesulfonic acid in anhydrous dioxane. After standing for 25 minutes at room temperature, methanolic ammonia is added until the solution is slightly basic. The solvent is removed under reduced pressure and the residual oil dissolved in ether. The ether solution is washed with an aqueous sodium bicarbonate solution, dried over sodium sulfate and concentrated to a small volume. Crystallization of the residue yields 4,6α,17α-trimethyl-17β,19-di(2'-tetrahydropyranyloxy)-4-androsten-3-one.

Substituting 19-hydroxy-6α-methyl-4-androstene-3,17-dione for the 17β,19-dihydroxy-4,6α,17α-trimethyl-4-androsten-3-one above results in the preparation of 6α-methyl-19-(2'-tetrahydropyranyloxy)-4-androsten-3,17-dione.

EXAMPLE 40

4,6α,17α-Trimethyl-17β,19-di(2'-tetrahydropyranyloxy)-5α-androstan-3-one

A solution of 4,6α,17α-trimethyl-17β,19-di(2'-tetrahydropyranyloxy)-4-androsten-3-one in anhydrous tetrahydrofuran is added with stirring to a solution of lithium in liquid ammonia. After 10 minutes the blue color is discharged with solid ammonium chloride. The residue obtained after evaporation of the ammonia is treated with water and the resulting mixture extracted with ethyl acetate. The ethyl acetate solution is washed well with water, dried over sodium sulfate and concentrated under vacuum. The residue so obtained is dissolved in acetone and oxidized with Jones reagent at 10° C. for about 10 minutes. Water is added to the acetone layer and the solid product which forms is collected by filtration. Crystallization from hexane yields 4,6α,17α-trimethyl-17β,19-di(2'-tetrahydropyranyloxy)-5α-androstan-3-one.

Substituting 17β-hydroxy-4,6α,17α-trimethyl-4-androstene-3,19-dione, 17β-hydroxy-4,6α,17α-trimethyl-4-androstene-3,19-dione acetate, 19-tetrahydropyranyloxy-4-androstene-3,17-dione, 19-trimethylsiloxy-4-androstene-3,17-dione and 6α-methyl-19-(2'-tetrahydropyranyloxy)-4-androstene-3,17-dione for the 4,6α,17α-trimethyl-17β,19-di(2'-tetrahydropyranyloxy)-4-androsten-3-one above results in the preparation of 17β-hydroxy-4,6α,17α-trimethyl-5α-androstane-3,19-dione, 17β-hydroxy-4,6α,17α-trimethyl-5α-androstane-3,19-dione acetate, 19-tetrahydropyranyloxy-5α-androstane-3,17-dione, 19-trimethylsiloxy-5α-androstane-3,17-dione and 6α-methyl-19-(2'-tetrahydropyranyloxy)-5α-androstane-3,17-dione, respectively.

EXAMPLE 41

17β,19-Dihydroxy-4,17α-dimethyl-4-androsten-3-one

A solution of 17β,19-dihydroxy-17α-methyl-4-androsten-3-one in t-butanol is heated to boiling and added to a boiling solution of potassium t-butoxide in t-butanol. Methyl chloride in t-butanol is added slowly. The solution is cooled, acidified with concentrated hydrochloric acid, and diluted with water. The t-butanol is removed under vacuum and the aqueous layer extracted with ethylacetate. The extract is washed with water, dried over magnesium sulfate and evaporated in vacuo. The residue so obtained is chromatographed on silica gel and eluted with ethylacetate. The eluant is evaporated to dryness and the residue crystallized from acetonitrile to yield 17β,19-dihydroxy-4,17α-dimethyl-4-androstene-3-one.

EXAMPLE 42

17β-Hydroxy-4,17α-dimethyl-4-androstene-3,19-dione

To a solution of 17β,19-dihydroxy-4,17α-dimethyl-4-androsten-3-one in acetone at 25° C. is added with stirring one equivalent of Jones reagent. After standing for 15 minutes the upper acetone layer is decanted and poured onto ice water with vigorous stirring. The precipitate is removed by vacuum filtration, washed well with water and dissolved in ether. The ether solution is dried over magnesium sulfate and the ether removed in vacuo. The residue is crystallized from an acetone-hexane solution to yield 17β-hydroxy-4,17α-dimethyl-4-androstene-3,19-dione.

EXAMPLE 43

17β-Hydroxy-4α,17α-dimethyl-5α-androstane-3,19-dione

A solution of 17β-hydroxy-4,17α-dimethyl-4-androstene-3,19-dione in anhydrous dioxane and ether is rapidly added to a stirred solution of lithium in liquid ammonia. After standing for 10 minutes solid ammonium chloride is added to discharge the blue color and the ammonia evaporated. The residue is dissolved in chloroform, washed with water, dried over magnesium sulfate and evaporated to dryness. This residue is dissolved in acetone and oxidized with Jones reagent at 10° C. for 5 minutes. Water is added to the reaction mixture and the precipitate which forms is filtered. Crystallization of this precipitate from a pentane-ether solution yields 17β-hydroxy-4α,17α-dimethyl-5α-androstane-3,19-dione.

Substituting 4,17α-dimethyl-17β,19-di(4'-tetrahydropyranyloxy)-4-androsten-3-one for the 17β-hydroxy-4,17α-dimethyl-4-androstene-3,19-dione above results in the preparation of 4α,17α-dimethyl-17β,19-di(4'-tetrahydropyranyloxy)-5α-androstan-3-one.

EXAMPLE 44

4,17α-Dimethyl-17β,19-di(4'-tetrahydropyranyloxy)-4-androsten-3-one

17β,19-Dihydroxy-4,17α-dimethyl-4-androsten-3-one is dissolved in dimethylformamide and heated to 50° C. The compound 4-bromotetrahydropyran is added, followed by the addition of sodium hydride. Heating and stirring is continued for a period of about 4 hours and the cooled reaction mixture is poured onto ice water. The oil is extracted with ether and the ether extracts are washed well with water, dried over magnesium sulfate and concentrated to leave a solid residue. Crystallization of this residue from a hexane solution yields 4,17α-dimethyl-17β,19-di(4'-tetrahydropyranyloxy)-4-androsten-3-one.

EXAMPLE 45

4α,17α-Dimethyl-5α-androstane-3β,17β,19-triol

To an ether solution of 17β-hydroxy-4α,17α-dimethyl-5α-androstane-3,19-dione is added a suspension of lithium aluminum hydride in ether. After refluxing for 1 hour, water is added cautiously, the ether layer is separated, dried over magnesium sulfate and evaporated under reduced pressure. Crystallization of the residue from an acetone-hexane solution yields 4α,17α-dimethyl-5α-androstane-3β,17β,19-triol.

EXAMPLE 46

4α-Methyl-17β,19-di(triphenylsiloxy)-5α-androstan-3-one

A solution of 17β,19-di(triphenylsiloxy)-4-androsten-3-one in anhydrous tetrahydrofuran is added to a stirred solution of lithium in liquid ammonia. After stirring for a period of about 25 minutes, a solution of methyliodide in tetrahydrofuran is added dropwise and stirring continued for an additional hour following which an additional quantity of methyliodide in tetrahydrofuran is added. The resulting mixture is stirred overnight allowing the ammonia to evaporate. The residue is treated with water and ethyl acetate. The ethyl acetate layer is dried over magnesium sulfate and the solvent removed. Crystallization of the residue from a solution of hexane yields 4α-methyl-17β, 19-di(triphenylsiloxy)-5α-androsten-3-one.

EXAMPLE 47

5α,6α-Epoxy-17α-methyl-androstane-3β,17β,19-triol 3,19-diacetate

A solution of 17α-methyl-5-androstene-3β,17β,19-triol 3,19-diacetate in chloroform is chilled to 0° C. and treated with m-chloroperbenzoic acid in chloroform which is precooled to 0° C. The mixture is stirred and allowed to warm to room temperature. After 48 hours the solution is washed with a 10% sodium sulfite solution, an sodium thiosulfate solution, a sodium bicarbonate solution and finally with water. The chloroform extract is dried over magnesium sulfate and evaporated in vacuo. The residue is crystallized from methanol to yield 5α,6α-epoxy-17α-methylandrostane-3β,17β,19-triol 3,19-diacetate.

EXAMPLE 48

6β,17α-Dimethylandrostane-3β,5α,17β,19-tetrol

Ethereal methylmagnesium bromide is slowly added to a stirred solution of 5α,6α-epoxy-17α-methylandrostane-3β,17β,19-triol in tetrahydrofuran. The solution is heated at its reflux temperature for about 24 hours, cooled, and poured onto a saturated aqueous ammonium chloride solution. The resultant solution is extracted with ethylacetate, washed with brine, dried over magnesium sulfate and the solvent removed under reduced pressure. The residue is crystallized from ethyl acetate to yield 6β,17α-dimethyl-androstane-3β,5α,17β,19-tetrol.

EXAMPLE 49

17β-Hydroxy-6α,17α-dimethyl-4-androstene-3,19-dione

6β,17α-Dimethylandrostane-3β,5α,17β,19-tetrol is dissolved in acetone and two equivalents of Jones Reagent are added with stirring. After standing for 15 minutes the reaction mixture is poured onto water and stirred for an additional 30 minutes. The solid which forms is filtered and dissolved in methanol containing sodium hydroxide. After standing for 2 hours the methanol is removed at room temperature and the residue triturated with water. Recrystallization of this residue from an acetone-water solution yields 17β-hydroxy-6α,17α-dimethyl-4-androstene-3,19dione.

EXAMPLE 50

17β-Hydroxy-6α,17α-dimethyl-5α-androstane-3,19-dione

A solution of 17β-hydroxy-6α,17α-dimethyl-4-androstene-3,19-dione in anhydrous tetrahydrofuran is added to a solution of lithium in liquid ammonia. After stirring for 10 minutes, the blue color is discharged with solid ammonium chloride. The residue obtained after evaporation of the ammonia is treated with water and ethyl acetate. The ethyl acetate layer is dried over magnesium sulfate and the solvent removed. The crude product is dissolved in acetone and chilled to 10° C. and Jones reagent added thereto. After stirring for about 5 minutes, the reaction mixture is poured onto water and the product extracted with ethyl acetate. The ethyl acetate extract is washed with water, dried over magnesium sulfate and concentrated under reduced pressure. Crystallization from a hexane solution furnishes the desired 17β-hydroxy-6α,17α-dimethyl-5α-androstane-3,19-dione.

EXAMPLE 51

6α,17α-Dimethyl-4-androstene-3β,17β,19-triol

Sodium borohydride is added under nitrogen with stirring to a solution of 17β-hydroxy-6α,17α-dimethyl-4-androstene-3,19-dione in methanol. After stirring for 5 hours at room temperature, the solution is poured onto water which contains a few drops of acetic acid. The solid which forms is filtered and crystallized from methanol to yield 6α,17α-dimethyl-4-androstene-3β,17β,19-triol.

EXAMPLE 52

17β,19-Dihydroxy-6α,17α-dimethyl-4-androsten-3-one

6α,17α-Dimethyl-4-androsten-3β,17β,19-triol is dissolved in hot chloroform and cooled to 15° C. Activated manganese dioxide is added at a rate such that the temperature does not rise above 25° C. Stirring is continued at room temperature for about 1 hour. The manganese dioxide is removed by filtration through diatomaceous earth and the chloroform distilled off under vacuum. The residue which remains is crystallized from acetonitrile to yield 17β,19-dihydroxy-6α,17α-dimethyl-4-androsten-3-one.

EXAMPLE 53

6,17α-Dimethyl-3-methoxy-3,5-androstadiene-17β,19-diol diacetate

17β,19-Dihydroxy-6α,17α-dimethyl-4-androsten-3-one is dissolved in a mixture of acetic anhydride and pyridine and the solution allowed to stand overnight at room temperature. The solvents are removed under vacuum and the remaining residue is crystallized from a solution of acetone-hexane to yield 17β,19-dihydroxy-6α,17α-dimethyl-4-androsten-3-one diacetate. This product is stirred with trimethylorthoformate, p-toluenesulfonic acid and methanol in tetrahydrofuran for about 2 hours at room temperature, poured onto ice water containing a few drops of pyridine and stirred well. The solid which forms is filtered and crystallized from methanol to yield pure 6,17α-dimethyl-3-methoxy-3,5-androstadiene-17β,19-diol diacetate.

EXAMPLE 54

17β,19-Dihydroxy-6α,17α-dimethyl-5α-androstan-3-one diacetate

A solution of 6,17α-dimethyl-3-methoxy-3,5-androstadiene-17β,19-diol diacetate in ethyl acetate is hydrogenated with platinum oxide at atmospheric pressure. The solution is filtered and the solvent removed under reduced pressure. The residue is dissolved in aqueous methanol containing a drop of hydrochloric acid and stirred for 20 minutes at room temperature. The methanol is removed and replaced with ether. The ether extract is washed with water, dried over magnesium sulfate and concentrated to dryness. Crystallization of the residue from an ether-hexane solution yields 17β,19-dihydroxy-6α,17α-dimethyl-5α-androstan-3-one diacetate.

EXAMPLE 55

19-Acetoxy-5α,6α-epoxy-androstane-3,17-dione bis ethyleneketal

To a solution of 19-acetoxy-5-androstene-3,17-dione bis ethyleneketal in methylenechloride which has been precooled to 0° C., is added a precooled methylenechloride solution of m-chloroperbenzoic acid also at 0° C. The resulting mixture is stirred at room temperature for about 24 hours and additional methylenechloride is added. The solution is washed sequentially with solutions of sodium sulfite, sodium thiosulfate, sodium bicarbonate and finally with water. The methylenechloride extract is dried over magnesium sulfate and evaporated to dryness under reduced pressure. Recrystallization of this residue from methanol yields 19-acetoxy-5α,6α-epoxy-androstane-3,17-dione bis ethyleneketal.

EXAMPLE 56

5α,19-Dihydroxy-6β-methylandrostane-3,17-dione bis ethyleneketal

To a solution of 19-acetoxy-5α,6α-epoxyandrostane-3,17-dione bis ethyleneketal in tetrahydrofuran is added an ethereal solution of methylmagnesium bromide. The resultant mixture is refluxed for a period of about 4 hours, cooled and treated with a saturated aqueous ammonium chloride solution. The organic layer is evaporated, extracted with ethyl acetate, washed with brine, dried over magnesium sulfate and concentrated to dryness. Crystallization of the residue from a solution of acetone-hexane yields 5α,19-dihydroxy-6β-methylandrostane-3,17-dione bis ethylenektal.

EXAMPLE 57

19-Hydroxy-6α-methyl-4-androstene-3,17-dione

A solution of 5α,19-dihydroxy-6β-methylandrostane-3,17-dione bis ethylenektal in methanol containing aqueous sulfuric acid is heated to its reflux temperature. The solvent is subsequently removed. Crystallization of the residue from an acetone-hexane solution yields 19-hydroxy-6α-methyl-4-androstene-3,17-dione.

EXAMPLE 58

19-Hydroxy-6-methyl-5-androstene-3,17-dione bis ethyleneketal acetate

5α,19-Dihydroxy-6β-methylandrostane-3,17-dione bis ethyleneketal is stirred overnight in a solution of acetic anhydride and pyridine. The solvents are removed under reduced pressure and the residue triturated with ice water. The solid which results is filtered, air dried and crystallized from an ether-hexane solution to yield 5α,19-dihydroxy-6β-methylandrostane-3,17-dione bis ethyleneketal 19-acetate. This material is dissolved in ether and phosphorous oxychloride and triethylamine are added with stirring. After about 30 minutes water is added to this mixture. The ether layer is separated, dried over magnesium sulfate and concentrated in vacuo. The residue so obtained is crystallized from an ether-hexane solution to yield 19-hydroxy-6-methyl-5-androstene-3,17-dione bis ethyleneketal acetate.

EXAMPLE 59

19-Hydroxy-6β-methyl-5α-androstane-3,17-dione acetate

A solution of 19-hydroxy-6-methyl-5-androstene-3,17-dione bis ethylenektal acetate in methanol is hydrogenated with a 10% palladium-on-charcoal catalyst at atmospheric pressure for a period of about 8 hours. After filtration of the catalyst, additional methanol and aqueous hydrochloric acid are added to the filtrate and the solution is heated to its reflux temperature. After about 30 minutes, the solution is poured onto water, and the solid which separates is filtered and air dried. Crystallization of this solid from an ether-hexane solution yields 19-hydroxy-6β-methyl-5α-androstane-3,17-dione acetate.

EXAMPLE 60

4,6-Androstadiene-3,17,19-trione

19-Hydroxy-4-androstene-3,17-dione and chloranil are dissolved in t-butanol which is rapidly brought to its reflux temperature. The t-butanol is removed by distillation at atmospheric pressure at such a rate that the reflux time and distillation time approximate one hour. The dark pasty residue is triturated with hot chloroform and cooled. The solid residue is removed by filtration and the filtrate extracted with water, followed by a 2% sodium hydroxide solution, washed with water, dried over magnesium sulfate and the solvent removed under vacuum to yield 19-hydroxy-4,6-androstadiene-3,17-dione. The diene so obtained is dissolved in acetone and chilled in an ice bath. Jones reagent is added over a period of 10 minutes and stirring continued for an additional 45 minutes. The mixture is poured onto water. The solid which separates is filtered and recrystallized from benzene to yield 4,6-androstadiene-3,17,19-trione.

Substituting 19-hydroxy-4-methyl-4-androstene-3,17-dione for the 19-hydroxy-4-androstene-3,17-dione above results in the preparation of 4-methyl-4,6-androstadiene-3,17,19-trione.

EXAMPLE 61

7α-Methyl-5-androstene-3,17,19-trione

A solution of lithium dimethylcopper is prepared under nitrogen by the addition of 1.6 M ethereal methyllithium to a slurry of cuprous iodide in anhydrous ether at 0° C. The solution is stirred at 0° C. for 20 minutes and the compound 4,6-androstadiene-3,17,19-trione in anhydrous tetrahydrofuran is added over 20 minutes and stirred for an additional 30 minutes. The mixture is poured onto a saturated aqueous ammonium chloride solution, benzene is added and the resulting mixture is rapidly filtered through diatomaceous earth. The organic layer is washed with an aqueous ammonium chloride solution, washed with water, dried over magnesium sulfate and evaporated to dryness. The crude product is dissolved in a minimum volume of methylenechloride and rapidly chromatographed on a short column of silica gel packed in methylenechloride. The eluant is evaporated to dryness and the residue crystallized from an acetone-hexane solution to yield 7α-methyl-5-androstene-3,17,19-trione.

EXAMPLE 62

7α-Methyl-5α-androstane-3,17,19-trione

A solution of 7α-methyl-5-androstene-3,17,19-trione in ethanol is hydrogenated with 5% palladium on charcoal. The catalyst is removed by filtration and the resulting solution evaporated to dryness. Crystallization of the residue from a pentane-ether solution results in the preparation of 7α-methyl-5α-androstane-3,17,19-trione.

EXAMPLE 63

17α-Methyl-5α-androstane-17β,19-diol

17β,19-Dihydroxy-17α-methyl-5α-androstan-3-one in acetic acid is treated with ethanedithiol and p-toluenesulfonic acid. After standing for 4 hours at room temperature, the solution is poured onto water and the mixture extracted with methylenechloride. The methylenechloride extract is washed well with water, washed with a sodium hydroxide solution, washed again with water, dried over sodium sulfate and evaporated under reduced pressure to leave a residue of 17β,19-dihydroxy-17α-methyl-5α-androstan-3-one 3-ethylenethioketal which is crystallized once from a solution of acetone-hexane.

Raney nickel is added to a solution of 17β,19-dihydroxy-17α-methyl-5α-androstan-3-one 3-ethylenethioketal in methanol and the resulting suspension is refluxed for 4 hours with rapid stirring. The suspension is cooled, filtered, and the solvent evaporated. The residue is chromatographed on silica gel and eluted with methylenechloride. The eluate is evaporated to dryness and the residue recrystallized from an acetone-hexane solution to yield 17α-methyl-5α-androstane-17β,19-diol.

Substituting 1α,7α-dimethyl-17β,19-dihydroxy-5α-androstan-3-one, 4α,6α,17α-trimethyl-17β,19-di(2'-tetrahydropyranyloxy)-5α-androstan-3-one, 4α,17α-dimethyl-17β,19-di(4'-tetrahydropyranyloxy)-5α-androstan-3-one, 17β,19-dihydroxy-6α,17α-dimethyl-5α-androstan-3-one diacetate and 4α-methyl-17β,19-di(triphenylsiloxy)-5α-androstan-3-one for the 17β,19-dihydroxy-17α-methyl-5α-androstan-3-one above results in the preparation of 1α,7α-dimethyl-5α-androstan-17β,19-diol, 4α,6α,17α-trimethyl-17β,19-di(2'-tetrahydropyranyloxy)-5α-androstane, 4α,17α-dimethyl-17β,19-di(4'-tetrahydropyranyloxy)-5α-androstane, 6α,17α-dimethyl-5α-androstane-17β,19-diol diacetate and 4α-methyl-17β,19-di(triphenylsiloxy)-5α-androstane, respectively.

EXAMPLE 64

17β-Hydroxy-17α-methyl-5α-androstan-19-one

17α-Methyl-5α-androstan-17β,19-diol is dissolved in dimethylformamide at 40° C. and one equivalent of Jones reagent added all at one time. The mixture is stirred for about 5 hours at 40° C., cooled and a 1% aqueous sodium sulfate solution is added. After several hours the solid crystals are collected by filtration, washed with water and air dried. Crystallization from an acetone-hexane solution yields 17β-hydroxy-17α-methyl-5α-androstan-19-one.

Substituting 4α,6α,17α-trimethyl-5α-androstane-17β,19-diol and 6α,17α-dimethyl-5α-androstane-17β,19-diol for the 17α-methyl-5α-androstan-17β,19-diol above results in the preparation of 17β-hydroxy-4α,6α,17α-trimethyl-5α-androstan-19-one and 17β-hydroxy-6α,17α-dimethyl-5α-androstan-19-one, respectively.

EXAMPLE 65

1α-Methyl-5α-androstane-3α,17β,19-triol 19-acetate

A 1 M solution of lithium tri-sec-butylborohydride in tetrahydrofuran under nitrogen is cooled in a dry ice-acetone bath to about −78° C. and 19-hydroxy-1α-methyl-5α-androstane-3,17-dione acetate in tetrahydrofuran is slowly added. The reaction mixture is stirred for two hours at this temperature, warmed to 0° C. and stirring continued for an additional two hours. The reaction mixture is decomposed by the addition of a 3 N sodium hydroxide solution followed by the addition of a 30% hydrogen peroxide solution. Care is taken that the solution temperature remains below 10° C. during decomposition. Solid potassium carbonate is added to the reaction mixture and the tetrahydrofuran decanted therefrom. The solid residue is washed with tetrahydrofuran and the combined solutions are dried over sodium sulfate, filtered and evaporated to dryness. The residue is crystallized from an acetone-hexane solution to yield 1α-methyl-5α-androstane-3α,17β,19-triol 19-acetate.

Substituting 1α-methyl-17β,19-di(trimethylsiloxy)-5α-androstan-3-one, 19-trimethylsiloxy-5α-androstane-3,17-dione, 19-(2'-tetrahydropyranyloxy)-5α-androstane-3,17-dione and 19-hydroxy-6β-methyl-5α-androstane-3,17-dione acetate for the 19-hydroxy-1α-methyl-5α-androstane-3,17-dione acetate above results in the preparation of 1α-methyl-17β,19-di(trimethylsiloxy)-5α-androstan-3α-ol, 19-trimethylsiloxy-5α-androstane-3α,17β-diol, 19-(2'-tetrahydropyranyloxy)-5α-androstane-3α,17β-diol, and 6β-methyl-5α-androstane-3α,17β,19-triol 19-acetate.

EXAMPLE 66

19-Hydroxy-3β-(2'-tetrahydropyranyloxy)-5α-androstan-17-one acetate

A solution of 3β,19-dihydroxy-5α-androstan-17-one 19-acetate, p-toluenesulfonic acid and 2,3-dihydropyran are stirred for 3 hours at room temperature. The reaction solution is diluted with ether, washed with an aqueous sodium carbonate solution, washed with water, dried over sodium sulfate and evaporated to dryness under vacuum. Crystallization of the residue from an acetone-hexane solution results in the preparation of 19-hydroxy-3β-(2'-tetrahydropyranyloxy)-5α-androstan-17-one acetate.

Substituting 3β,19-dihydroxy-5α-androstan-17-one and 5α-androstan-3β,17β,19-triol for the 3β,19-dihydroxy-5α-androstan-17-one 19-acetate above results in the preparation of 3β,19-di(2'-tetrahydropyranyloxy)-5α-androstan-17-one and 3β,17β,19-tri(2'-tetrahydropyranyloxy)-5α-androstane, respectively.

EXAMPLE 67

19-Hydroxy-3β-(1'-methoxy-1'-cyclopentyloxy)-5α-androstan-17-one acetate

To a solution of 3β,19-dihydroxy-5α-androstan-17-one acetate in dioxane is added with stirring cyclopentanone methylenol ether and pyridine p-toluenesulfonate. A precipitate forms, which after standing overnight, is filtered. The precipitate, when crystallized from methanol yields 19-hydroxy-3β-(1'-methoxy-1'-cyclopentyloxy)-5α-androstan-17-one acetate.

Substituting 3β,19-dihydroxy-5α-androstan-17-one, 5α-androstane-3β,17β,19-triol, 3β,19-dihydroxy-5α-androstan-17-one 3-acetate, 3β,17β-dihydroxy-1β-methyl-5α-androstan-19-one and 3β-triphenylsiloxy-5α-androstane-17β,19-diol for the 3β,19-dihydroxy-5α-androstan-17-one 19-acetate above results in the preparation of 3β,19-di(1'-methoxy-1'-cyclopentyloxy)-5α-androstan-17-one, 3β,17β,19-tri-(1'-methoxy-1'-cyclopentyloxy)-5α-androstane, 3β-hydroxy-19-(1'-methoxy-1'-cyclopentyloxy)-5α-androstan-17-one acetate, 3β,17β-di(1'-methoxy-1'-cyclopentyloxy)-1β-methyl-5α-androstan-19-one and 17β,19-di(1'-methoxy-1'-cyclopentyloxy)-3β-triphenylsiloxy-5α-androstane, respectively.

EXAMPLE 68

3β-(1'-Cyclopentenyloxy)-19-hydroxy-5α-androstan-17-one acetate

A solution of 19-hydroxy-3β-(1'-methoxy-1'-cyclopentyloxy)-5α-androstan-17-one acetate in dimethylformamide containing a drop of pyridine is heated to its reflux temperature and the alcohol removed by distillation as it forms. After one hour, the remaining solvent is distilled under vacuum and the residue is crystallized from a solution of methanol to yield 3β-(1'-cyclopentenyloxy)-19-hydroxy-5α-androstan-17-one acetate.

Substituting 3β,19-di(1'-methoxy-1'-cyclopentyloxy)-5α-androsten-17-one, 3β,17β,19-tri(1'-methoxy-1'-cyclopentyloxy)-5α-androstane, 3β-hydroxy-19-(1'-methoxy-1'-cyclopentyloxy)-5α-androstan-17-one acetate, 3β,17β-di(1'-methoxy-1'-cyclopentyloxy)-1β-methyl-5α-androstan-19-one and 17β,19-di(1'-methoxy-1'-cyclopentyloxy)-3β-tri-phenylsiloxy-5α-androstane for the 19-hydroxy-3β-(1'-methoxy-1'-cyclopentyloxy)-5α-androstan-17-one acetate above results in the preparation of 3β,19-di(1'-cyclopentenyloxy)-5α-androstan-17-one, 3β,17β,19-tri(1'-cyclopentenyloxy)-5α-androstane, 19-(1'-cyclopentenyloxy)-3β-hydroxy-5α-androstan-17-one acetate, 3β,17β-di(1'-cyclo--pentenyloxy)-1β-methyl-5α-androstan-19-one and 17β,19-di(1'-cyclopentenyloxy)-3β-triphenylsiloxy-5α-androstane, respectively.

EXAMPLE 69

3β,17β-Dimethoxy-1β-methyl-19-(2'-tetrahydropyranyloxy)-5α-androstane

1β-Methyl-19-(2'-tetrahydropyranyloxy)-5α-androstane-3β,17β-diol is dissolved in methylenechloride to which trimethyloxonium fluoroborate is added. After stirring for two hours at room temperature, water is added. The methylenechloride layer is separated, dried over magnesium sulfate and concentrated. The residue upon crystallization from hexane yields 3β,17β-dimethoxy-1β-methyl-19-(2'-tetrahydropyranyloxy)-5α-androstane.

Substituting 1β-methyl-5α-androstane-3β,17β,19-triol 3,17-diacetate, 17α-methyl-5α-androstane-17β,19-diol, 19-hydroxy-3β-triphenylsiloxy-5α-androstan-17-one and 3β,17β-dihydroxy-5α-androstan-19-one for the 1β-methyl-19-2'-tetrahydropyranyloxy)-5α-androstane-3β,17β-diol above results in the preparation of 19-methoxy-1β-methyl-5α-androstane-3β,17β-diol diacetate, 17α-methyl-17β,19-dimethoxy-5α-androstane, 19-methoxy-3β-triphenylsiloxy-5α-androstan-17-one and 3β,17β-dimethoxy-5α-androstan-19-one, respectively.

EXAMPLE 70

19-Hydroxy-3β-(2'-tetrahydropyranyloxy)-5α-androstan-17-one

19-Hydroxy-3β-(2'-tetrahydropyranyloxy)-5α-androstan-17-one acetate is refluxed in aqueous methanol containing sodium carbonate for about 2 hours. The solution is concentrated, diluted with water and the precipitate which forms is removed by filtration and air dried. Crystallization from an acetone-hexane solution yields 19-hydroxy-3β-(2'-tetrahydropyranyloxy)-5α-androstan-17-one.

Substituting 3β-(1'-cyclopentenyloxy)-19-hydroxy-5α-androstan-17-one acetate, 19-hydroxy-3β-triphenylsiloxy-5α-androstan-17-one acetate and 19-methoxy-1β-methyl-5α-androstane-3β,17β-diol diacetate for the 19-hydroxy-3β-(2'-tetrahydropyranyloxy)-5α-androstan-17-one acetate above results in the preparation of 3β-(1'-cyclopentenyl-oxy)-19-hydroxy-5α-androstan-17-one, 19-hydroxy-3β-triphenylsiloxy-5α-androstan-17-one and 19-methoxy-1β-methyl-5α-androstane-3β,17β-diol, respectively.

EXAMPLE 71

3β-(2'-Tetrahydropyranyloxy)-5α-androstane-17,19-dione

To an acetone solution of 19-hydroxy-3β-(2'-tetrahydropyranyloxy)-5α-androstan-17-one chilled to 0° C. is added one equivalent of Jones reagent with stirring. After standing for 10 minutes the acetone layer is poured onto ice water with vigorous stirring. After about 1 hour the solid is collected by vacuum filtration, air dried and crystallized from a solution of hexane to yield 3β-(2'-tetrahydropyranyloxy)-5α-androstane-17,19-dione.

Substituting 3β-(1'-cyclopentenyloxy)-19-hydroxy-5α-androstan-17-one and 19-methoxy-1β-methyl-5α-androstane-3β,17β-diol for the 19-hydroxy-3β-(2'-tetrahydropyranyloxy)-5α-androstan-17-one above results in the preparation of 3β-(1'-cyclopentenyloxy)-5α-androstane-17,19-dione and 19-methoxy-1β-methyl-5α-androstane-3,17-dione, respectively.

EXAMPLE 72

The following Example is illustrative of the behavioral activity for the compounds of this invention.

Copulatory behavioral tests are conducted in mature, sexually experienced Sprague-Dawley male rats that were either intact or castrated-adrenalectomized. Castration and adrenalectomy reduces the effect on behavior associated with endogenous steroids and/or their metabolites. The onset and intensity of behavioral responses related to mounting, intromission and ejaculation are determined both prior to and after an interval of at least two weeks postsurgery. Five animals per group are subcutaneously administered 500 micrograms/kg of 17β,19-dihydroxy-5α-androstan-3-one diacetate, testosterone or 0.25 ml/kg of olive oil vehicle for a period of 14 days. Ten minute behavioral observations are made in the presence of a receptive female rat on days 2, 8, 12 and 15 of the treatment period.

As shown in the table below at least two weeks after castration and adrenalectomy both the intromission frequency and the percent of animals responding is very low in comparison to their former intact state. Following testosterone treatment the castrated-adrenalectomized rats approach their pre-surgical sexual pattern of behavior after about 8 days of treatment. Castrated-adrenalectomized rats treated with 17β,19-dihydroxy-5α-androstan-3-one diacetate approach their pre-surgical sexual pattern of behavior after about day 8 of treatment. More importantly, the somatic androgenic effect upon the sex accessory organs of immature castrated rats receiving 17β,19-dihydroxy-5α-androstan-3-one diacetate is considerably less than with similar animals receiving testosterone and 5α-dihydrotestosterone.

MEAN NUMBER OF INTROMISSIONS AND PERCENT OF RATS DISPLAYING INTROMISSION PER 10 MINUTE OBSERVATION PERIOD

| Treatment | Pre-Treatment | | | | Treatment Period (14 days) | | | | | | | |
|---|---|---|---|---|---|---|---|---|---|---|---|---|
| | Pre Surgery | | Post Surgery | | 2nd Day | | 8th Day | | 12th Day | | 15th Day | |
| | No. | % | No. | % | No. | % | No | % | No. | % | No. | % |
| ADRENALECTOMIZED - CASTRATED | | | | | | | | | | | | |
| Vehicle (Olive Oil) | 15.6 | 100 | 2.4 | 20 | 3.4 | 20 | 0.0 | 0 | *NT | | 4.0 | 20 |
| Testosterone 500 μg/kg s.c. | 17.2 | 100 | 0.6 | 40 | 2.8 | 80 | 11.4 | 100 | *NT | | 19.8 | 100 |
| 5α-Dihydrotestosterone 500 μg/kg s.c. | 11.6 | 100 | 0.0 | 0 | 0.0 | 0 | 2.0 | 40 | 0.0 | 0 | 0.8 | 25 |
| 17β,19-dihydroxy-5α androstan-3-one diacetate 500 μg/kg s.c. | 15.4 | 100 | 0.8 | 25 | 13.5 | 100 | 12.5 | 100 | *NT | | 5.5 | 75 |
| INTACT | | | | | | | | | | | | |
| Vehicle (Olive Oil) | 12.6 | 100 | 16.2 | 80 | 19.0 | 100 | 20.8 | 100 | *NT | | 19.6 | 100 |

*NT = Not Tested

EXAMPLE 73

Preparation of a tablet formulation

One thousand tablets for oral use, each containing 25 mg of 17β-(4'-tetrahydropyranyloxy)-5α-androstane-3,19-dione are prepared according to the following formulation:

| | | |
|---|---|---|
| (a) 17β-(4'-tetrahydropyranyloxy)-5α-androstane-3,19-dione | | 25 |
| (b) Dicalcium phosphate | | 150 |
| (c) Methylcellulose, U.S.P. (15 cps) | | 6.5 |
| (d) Talc | | 20 |
| (e) Calcium stearate | | 2.5 |

The 17β-(4'-tetrahydropyranyloxy)-5α-androstane-3,19-dione and dicalcium phosphate are mixed well, granulated with a 7.5% aqueous solution of methylcellulose, passed through a No. 8 screen and carefully dried. The dried granules are passed through a No. 12 screen, blended with talc and calcium stearate and compressed into tablets.

EXAMPLE 74

Preparation of a capsule formulation

One thousand two-piece hard gelatin capsules for oral use each containing 10 mg of 17β-(1'-ethoxycyclohexyloxy)-5α-androstane-3,19-diol are prepared from the following ingredients:

| | Gm |
|---|---|
| (a) 17β-(1'-ethoxycyclohexyloxy)-5α-androstane-3,19-diol | 10 |
| (b) Lactose, U.S.P. | 100 |
| (c) Starch, U.S.P. | 10 |
| (d) Talc, U.S.P. | 5 |
| (e) Calcium stearate | 1 |

The finely powdered materials are mixed until uniformly dispersed and filled into hard shelled gelatin capsules of the appropriate size.

In a similar fashion one-piece soft gelatin capsules can be prepared in which the above formulation can be granulated, slugged or compressed directly into a rotary die or plate mold in which the capsule is formed. Alternatively, the above excipients may be omitted and the active ingredient dispensed as a powder directly into the capsule.

EXAMPLE 75

Preparation of an intramuscular injection

A sterile aqueous suspension suitable for intramuscular injection is prepared from the following ingredients:

| | Gm |
|---|---|
| (a) 17α-ethynyl-17β,19-di(trimethylsiloxy)-5α-androstane-3-one | 1 |
| (b) Polyethylene glycol 4000, U.S.P. | 3 |
| (c) Sodium chloride | 0.9 |
| (d) Polyoxyethylene derivatives of sorbitan monooleate (TWEEN 80) U.S.P. | 0.4 |
| (e) Sodium metabisulfite | 0.1 |
| (f) Methylparaben, U.S.P. | 0.18 |
| (g) Propylparaben, U.S.P. | 0.02 |
| (h) Water for injection q.s. to 100 ml | |

The parabens, sodium metabisulfite and sodium chloride are dissolved in approximately one-half the volume of water for injection at 80° C. with stirring. The solution is cooled to below 40° C. and the active ingredient is dissolved therein followed by the polyethylene glycol 4,000 and polyoxyethylene derivatives of sorbitan monooleate. The cooled solution is adjusted to the final volume with water for injection and is then sterilized by sterile filtration through a suitable filter. Each one ml of solution contains 10 mg of 17α-ethynyl-17β,19-di(trimethylsiloxy)-5α-androstan-3-one as the active ingredient.

We claim:

1. A method of enhancing the libido of mammals in need thereof which comprises the administration to such mammals of a therapeutically effective amount of a 19-oxygenated-5α-androstane having the formula

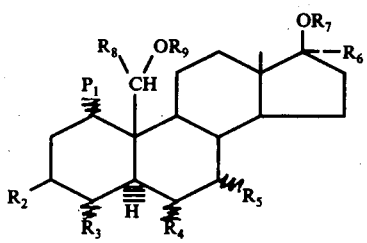

wherein $R_1$, $R_3$, $R_4$ and $R_5$ are hydrogen and methyl, $R_2$ is selected from the group consisting of $H_2$, oxo and $H(OR_{10})$, $R_6$ is selected from the group consisting of hydrogen, lower alkyl having from 1 to 6 carbon atoms, lower alkenyl having from 2 to 6 carbon atoms, lower alkynyl having from 2 to 6 carbon atoms and when taken together with $OR_7$ is oxo, $R_7$, $R_9$ and $R_{10}$ are each selected from the group consisting of hydrogen, acyl having from 1 to 12 carbon atoms and an ether selected from the group consisting of lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms, $R_8$ is hydrogen and when taken together with $OR_9$ is oxo.

2. A method according to claim 1 in which the mammals are primates.

3. A method of improving psychic attitudes associated with a diminished libido for primates in need thereof which comprises the administration to such primates of a therapeutically effective amount of a 19-oxygenated-5α-androstane of claim 1.

4. A method according to claim 1 in which the 19-oxygenated-5α-androstane is administered in a total daily dose of from 0.1 milligrams to 3 grams.

* * * * *

UNITED STATES PATENT AND TRADEMARK OFFICE
CERTIFICATE OF CORRECTION

PATENT NO. : 4,071,625

DATED : January 31, 1978

INVENTOR(S) : Joyce F. Grunwell and Vladimir Petrow

It is certified that error appears in the above-identified patent and that said Letters Patent are hereby corrected as shown below:

Column 3, line 51, "17;62-propoxy-" should read "17β-propoxy-"; Column 3, line 60, "17α-" should read "17β-"; Column 4, line 5, "7;60-" should read "7α-"; Column 4, line 7, "7α,17;60-" should read "7α,17α-"; Column 4, line 15, "-17;62-" should read "-17β-"; Column 4, line 19, "-17;62-" should read "-17β-"; Column 4, lines 20-21, "17;62-ethoxy-17;60-" should read "17β-ethoxy-17α-"; Column 6, line 62, "3-ol" should read "3β-ol"; Column 7, line 20, "Atwater3 s" should read "Atwater's"; Column 8, line 37, "17α,19-" should read "17β,19-"; Column 8, lines 62-64, "3,17-diacetate. In the same manner 3β,19-oxidoandrostane 3,17-diacetate. In the same manner 3β-hydroxyandrost-5-en-17-one" should read "3,17-diacetate. In the same manner 3β-hydroxyandrost-5-en-17-one"; Column 10, line 21, "17β-" should read "17α-"; Column 15, line 7, "5β-" should read "5α-"; Column 21, line 2, "-3β,19β-" should read "-3β,17β-"; Column 22, line 36, "1β,7β-" should read "1β,7α-"; Column 23, line 1, "1α,7β-" should read "1β,7α-"; Column 23, line 4, "1,62,7α" should read "1β,7α"; Column 23, line 9, "methylandrostene" should read "methylandrostane"; Column 23, line 22, "methylandrostene" should read "methylandrostane"; Column 23, line 23, "androstene" should read "androstane"; Column 23, line 27, "dimethylandrostene" should read "dimethylandrostane"; Column 23, line 28, "dimethylandrostene" should read "dimethylandrostane"; Column 23, line 56,

UNITED STATES PATENT AND TRADEMARK OFFICE
CERTIFICATE OF CORRECTION

PATENT NO. : 4,071,625
DATED : January 31, 1978

Page 2 of 2

INVENTOR(S) : Joyce F. Grunwell and Vladimir Petrow

It is certified that error appears in the above-identified patent and that said Letters Patent are hereby corrected as shown below:

"-1,62,6α-" should read "-1β,6α-"; Column 24, line 8, "1,62,7α-" should read "1β,7α-"; Column 24, line 10, "3∫ diacetate" should read "3,17-diacetate".

Signed and Sealed this

Twenty-seventh Day of March 1979

[SEAL]

Attest:

RUTH C. MASON
Attesting Officer

DONALD W. BANNER
Commissioner of Patents and Trademarks